(12) United States Patent
Shelton, IV et al.

(10) Patent No.: US 6,978,921 B2
(45) Date of Patent: Dec. 27, 2005

(54) SURGICAL STAPLING INSTRUMENT INCORPORATING AN E-BEAM FIRING MECHANISM

(75) Inventors: Frederick E. Shelton, IV, Hillsboro, OH (US); Michael Earl Setser, Burlington, KY (US); William Bruce Weisenburgh, II, Maineville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 10/443,617

(22) Filed: May 20, 2003

(65) Prior Publication Data

US 2004/0232197 A1    Nov. 25, 2004

(51) Int. Cl.[7] ............................................. A61B 17/072
(52) U.S. Cl. .................... 227/176.1; 227/19; 227/180.1
(58) Field of Search .......................... 227/175.1, 175.2, 227/175.4

(56) References Cited

U.S. PATENT DOCUMENTS

| 5,031,814 | A |   | 7/1991  | Tompkins et al. |
|-----------|---|---|---------|-----------------|
| 5,071,052 | A |   | 12/1991 | Rodak et al.    |
| 5,137,198 | A |   | 8/1992  | Nobis et al.    |
| 5,397,046 | A |   | 3/1995  | Savage et al.   |
| 5,413,267 | A |   | 5/1995  | Solyntjes et al.|
| 5,413,268 | A |   | 5/1995  | Green et al.    |
| 5,445,304 | A |   | 8/1995  | Plyley et al.   |
| 5,465,895 | A |   | 11/1995 | Knodel et al.   |
| 5,484,095 | A |   | 1/1996  | Green et al.    |
| 5,535,937 | A |   | 7/1996  | Boiarski et al. |
| 5,584,425 | A |   | 12/1996 | Savage et al.   |
| 5,624,452 | A | * | 4/1997  | Yates .......................... 606/139 |
| 5,680,983 | A |   | 10/1997 | Plyley et al.   |
| 5,692,668 | A | * | 12/1997 | Schulze et al. .......... 227/175.1 |
| 5,709,334 | A |   | 1/1998  | Sorrentino et al.|
| 5,735,445 | A |   | 4/1998  | Vidal et al.    |
| 5,918,791 | A |   | 7/1999  | Sorrentino et al.|
| 6,010,054 | A |   | 1/2000  | Johnson et al.  |
| 6,032,849 | A |   | 3/2000  | Mastri et al.   |
| 6,079,606 | A |   | 6/2000  | Milliman et al. |
| 6,109,500 | A |   | 8/2000  | Alli et al.     |
| 6,786,382 | B1| * | 9/2004  | Hoffman ................... 227/178.1 |
| 2001/0029384 | A1 |   | 10/2001 | Nicholas et al. |
| 2001/0030219 | A1 | * | 10/2001 | Green et al.    |

* cited by examiner

Primary Examiner—Scott A. Smith
Assistant Examiner—Gloria R. Weeks
(74) Attorney, Agent, or Firm—Dean Garner

(57) ABSTRACT

A surgical severing and stapling instrument clamps, suitable for laparoscopic and endoscopic clinical procedures, clamps tissue within an end effector of an elongate channel pivotally opposed by an anvil. An E-beam firing bar moves distally through the clamped end effector to sever tissue and to drive staples on each side of the cut. The E-beam firing bar affirmatively spaces the spaces the anvil from the elongate channel to assure properly formed closed staples, especially when an amount of tissue is clamped that is inadequate to space the end effector. In particular, an upper pin of the firing bar longitudinally moves through an anvil slot and a channel clot is captured between a lower cap and a middle pin of the firing bar to assure a minimum spacing.

17 Claims, 17 Drawing Sheets

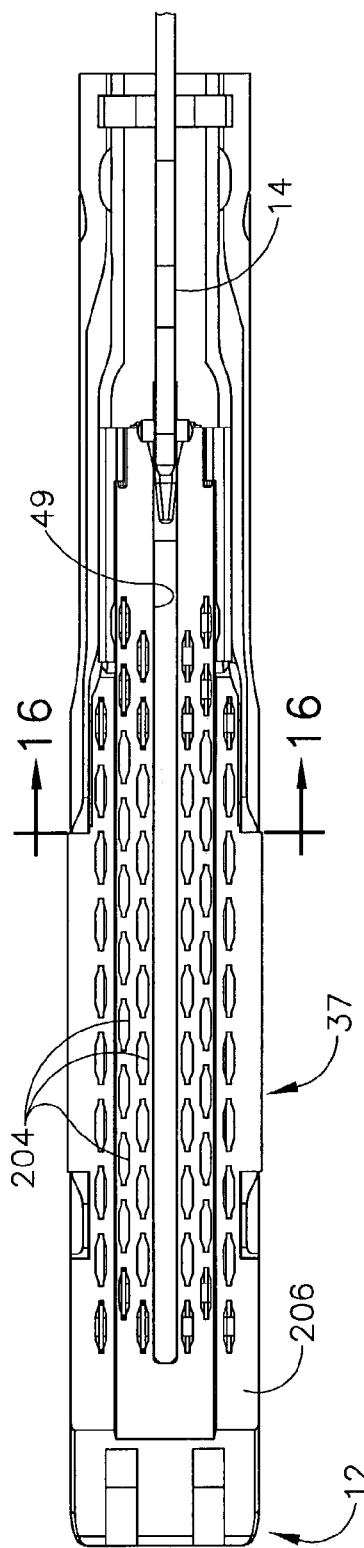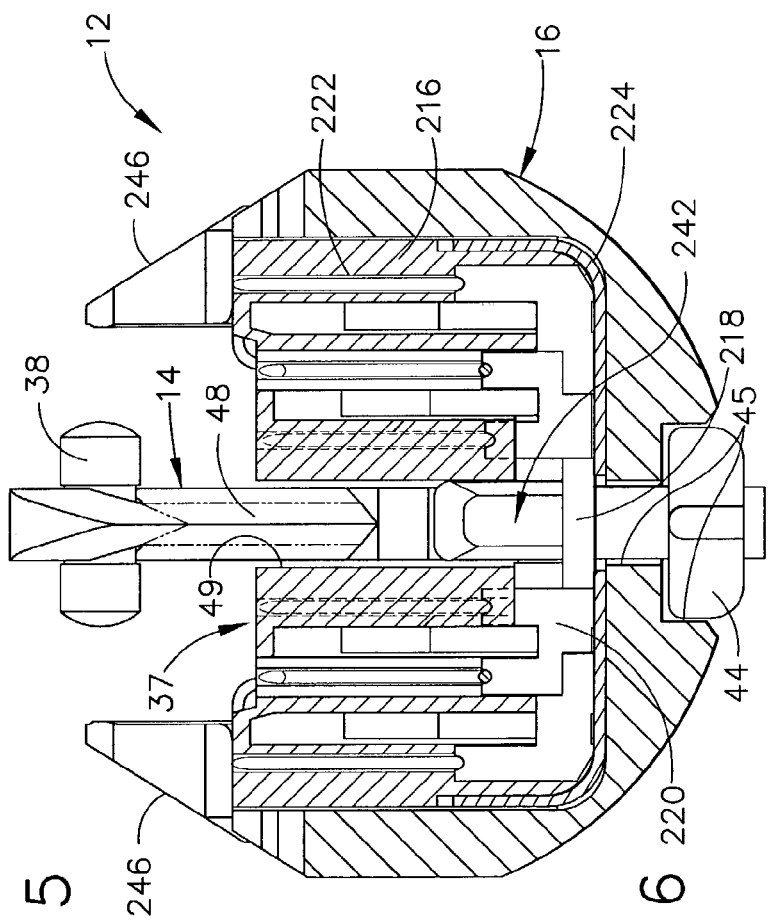

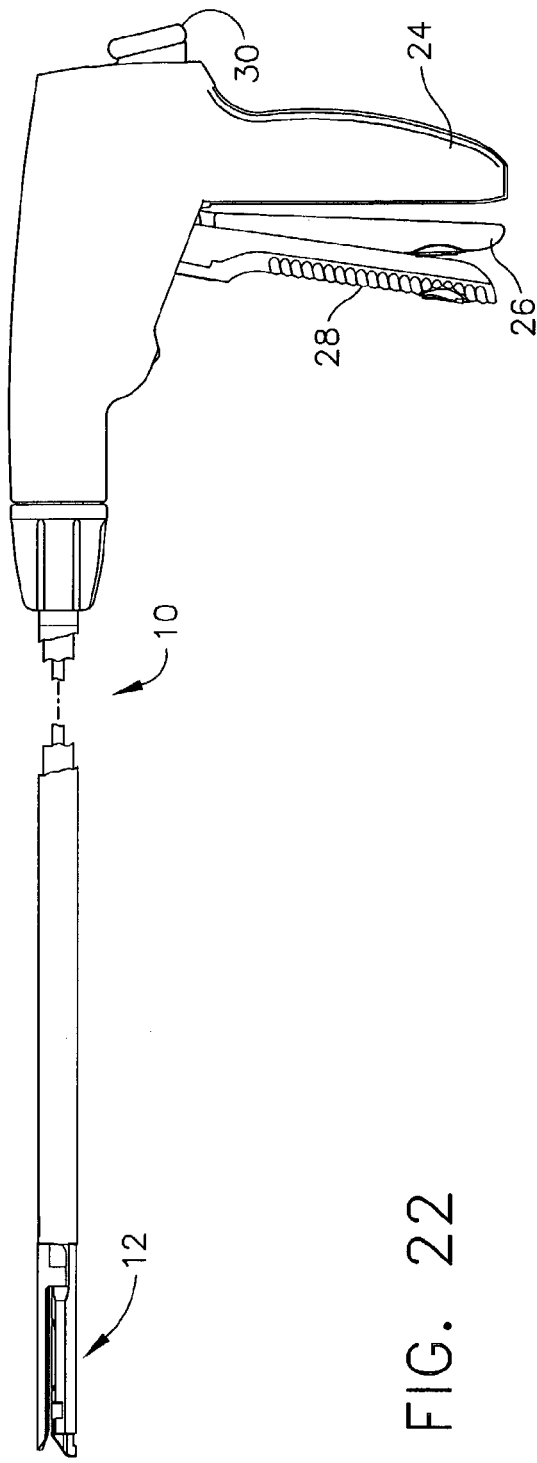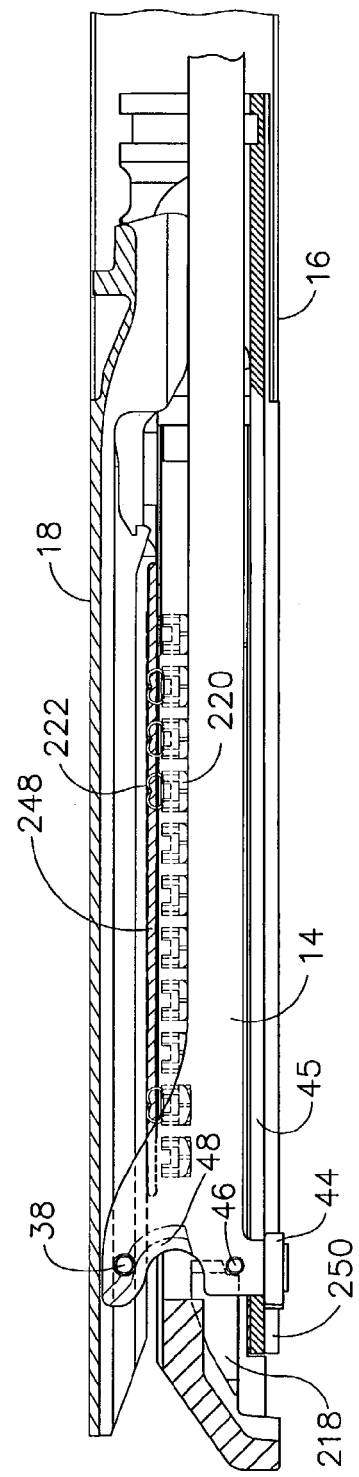

SURGICAL STAPLING INSTRUMENT INCORPORATING AN E-BEAM FIRING MECHANISM

CROSS REFERENCE TO RELATED APPLICATIONS

The present application is related to four co-pending and commonly-owned applications filed on even date herewith, the disclosure of each is hereby incorporated by reference in their entirety, these four applications being respectively entitled:
(1) "SURGICAL STAPLING INSTRUMENT HAVING A SINGLE LOCKOUT MECHANISM FOR PREVENTION OF FIRING" to Frederick E. Shelton IV, Mike Setser, and Bruce Weisenburgh;
(2) "SURGICAL STAPLING INSTRUMENT HAVING SEPARATE DISTINCT CLOSING & FIRING SYSTEMS" to Frederick E. Shelton, Mike Setser, and Brian J. Hemmelgarn;
(3) "SURGICAL STAPLING INSTRUMENT HAVING A SPENT CARTRIDGE LOCKOUT" to Frederick E. Shelton IV, Mike Setser, Bruce Weisenburgh; and
(4) "SURGICAL STAPLING INSTRUMENT HAVING A FIRING LOCKOUT FOR AN UNCLOSED ANVIL" to Frederick E. Shelton IV, Mike Setser, and Bruce Weisenburgh.

FIELD OF THE INVENTION

The present invention relates in general to surgical stapler instruments that are capable of applying lines of staples to tissue while cutting the tissue between those staple lines and, more particularly, to improvements relating to stapler instruments and improvements in processes for forming various components of such stapler instruments.

BACKGROUND OF THE INVENTION

Surgical staplers have been used in the prior art to simultaneously make a longitudinal incision in tissue and apply lines of staples on opposing sides of the incision. Such instruments commonly include a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

The simultaneous severing of tissue while forming rows of staples on each side of the cut reduces bleeding and simplifies the surgical procedure. However, an appropriate amount of tissue should be clamped between the jaws so that proper staple formation is achieved and so that a cutting member does not bind or otherwise fail to fully cut the clamped tissue.

A stapling and severing instrument that maintains a maximum jaw spacing is described in U.S. Pat. No. 4,429,695. In particular, a central knife carrier has an upper shoe that enters an upper passageway through an opening when the upper jaw is closed and has a lower shoe that is received within a lower passageway of the lower jaw. Thus, as the knife carrier is advanced distally, the shoes vertically and laterally position the upper and lower jaws. U.S. Pat. No. 4,429,695 teaches that the shoes are attached to the central knife carrier to resist vertical deflection (opening) of the jaws during ejection and forming of staples. As taught, the forces tend to vertically open the jaws during stapling. However, no mention is made of resisting forces that might be applied to vertically close the jaws. Additionally, this reference teaches that the device described therein is assembled from two separate, unconnected elements that are brought together and clamped onto tissue. The two elements form a device suitable only for an open procedure that has no size limitations.

Increasingly, endoscopic and laparoscopic procedures are preferred over open procedures due to their reduced post-operative recovery times and other advantages. Endoscopic stapling and severing instruments use a long slender jaw member that tends to deflect upwardly when clamped onto thick tissues. On thick tissue, this upward deflection of the free (distal) end of the jaw can cause differences in height of the formed staples as the distal gap between the anvil and cartridge is larger than the proximal gap. To ensure more uniform proximal to distal staple formation, the anvil is frequently cambered or bent inwardly toward the staple cartridge. This camber is better for thick tissue and can cause tighter staple forms at the distal end when used on thin tissue. To overcome this tight distal closure, pins or bumps have been added to the clamping surface of the cartridge adjacent to the distal end of the cartridge. The closure of the anvil onto the pin ensures a minimum gap at the distal end. However, surgeons were concerned about the pins or bumps causing tissue trauma. What is needed is a mechanism for maintaining a minimal gap between the anvil and cartridge and a mechanism for maintaining a maximum gap between the anvil and cartridge.

An example of a surgical stapler suitable for endoscopic applications is described in U.S. Pat. No. 5,465,895, which advantageously provides distinct closing and firing actions. Thereby, a clinician is able to close the jaw members upon tissue to position the tissue prior to firing. Once the clinician has determined that the jaw members are properly gripping tissue, the clinician can then fire the surgical stapler, thereby severing and stapling the tissue. The simultaneous severing and stapling avoids complications that may arise when performing such actions sequentially with different surgical tools that respectively only sever or staple.

One specific advantage of being able to close upon tissue before firing is that the clinician is able to verify via an endoscope that a sufficient amount of tissue has been captured between opposing jaws. Otherwise, opposing jaws may be drawn too close together, especially pinching at their distal ends, and thus not effectively forming closed staples in the severed tissue. Moreover, a firing bar that traverses between opposing jaws to sever the tissue and to drive the wedges that drive the staples may encounter resistance due to the pinched opposing jaws.

Thus, while such surgical staplers have been a significant advance in surgical procedures, an opportunity has been recognized for enhancing their effectiveness. In particular, it would be desirable to affirmatively maintain proper spacing between the opposing jaws during firing, both opening and closing deflections. In particular, endoscopic devices need to fit into an access device such a trocar, and must maintain a small shaft diameter. To date, no endoscopic stapling device has been provided that has room for a pair for longitudinal passageways for shoes on a cutter that resists both tensile and compressive jaw loadings.

Furthermore, it is desirable to maintain other advantages of U.S. Pat. No. 5,465,895 to include a wedge sled integral to a staple cartridge, rather than having camming surfaces attached to a cutter. Thereby, fabrication of the cutter is simplified, as is installation of the staple cartridge. Significantly, an integral wedge sled may be designed specifically for each size and application of a staple cartridge, allowing the stapling and severing instrument increased number of uses. In particular, the thickness of the staple cartridge may be based on the desired tissue thickness. Also, the number and spacing of rows of staples may vary.

Consequently, a significant need exists for an improved surgical stapling and severing instrument that maintains proper spacing in its end effector to achieve proper stapling of the severed tissue, yet retains the advantages of a staple cartridge having an integral wedge sled.

BRIEF SUMMARY OF THE INVENTION

The invention overcomes the above-noted and other deficiencies of the prior art by providing a firing mechanism that affirmatively vertically spaces an end effector of a surgical stapling and severing instrument. Thus, the instrument structurally assures adequate spacing to achieve proper stapling, even in instances where too little tissue is clamped in the end effector.

In one aspect of the invention, a surgical instrument includes a handle portion operable to produce a firing motion that actuates an implement portion. This implement portion has an elongate channel that receives a staple cartridge opposed by a pivotally attached anvil. A firing device includes a distally presented cutting edge longitudinally received between the elongate channel and the anvil, an upper member engageable to the anvil channel, a lower member engaging the channel slot, and a middle member operable to actuate the wedge sled, which is integral to the staple cartridge. The middle member advantageously opposes pinching of the end effector, assuring proper staple formation even when an otherwise too small amount of tissue has been clamped.

In another aspect of the invention, a surgical instrument is provided that is suitable for endo-surgical and laparoscopic procedures by have a diametrically sized end effector and shalt of the implement portion. A handle portion produces both a closing motion and firing motion that are transferred distally through the shaft of the implement portion. The firing mechanism responds to the firing motion by engaging both the anvil and the elongate channel to effect severing of clamped tissue and to affirmatively space the anvil and elongate channel to assure proper staple formation.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 15 depicts a section view of the end effector of the surgical stapling and severing instrument with the cartridge and firing bar in the start position taken along line 15—15 of FIG. 10.

FIG. 16 depicts a section view taken along line 16—16 of FIG. 15 showing the cross-sectional relationship between the firing bar, elongate channel, wedge sled, staple drivers, staples and staple cartridge.

FIG. 22 depicts a partially cut-away side elevation view of the surgical stapling and severing instrument of FIG. 1 in a fully fired position.

FIG. 23 depicts a view in centerline section of the distal end of the surgical stapling and severing instrument of FIG. 1 in a fully fired position.

DETAILED DESCRIPTION OF THE INVENTION

Figure 1:
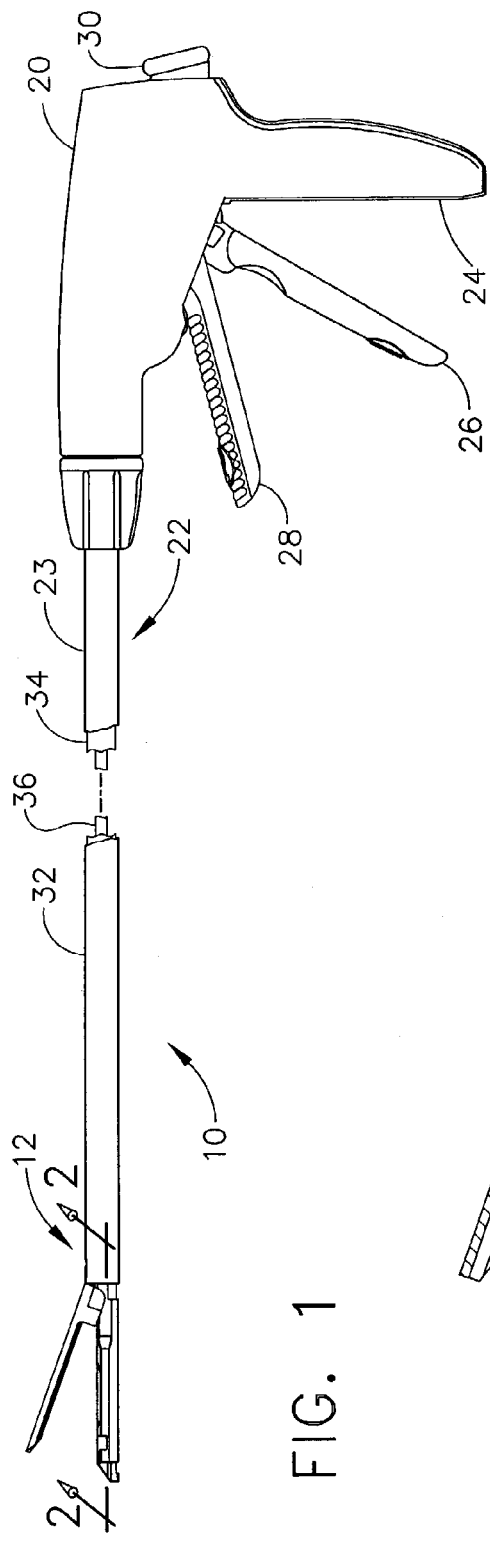
FIG. 1 depicts a partially cut-away side elevation view of a surgical stapling and severing instrument in an open position.
Figure 2:
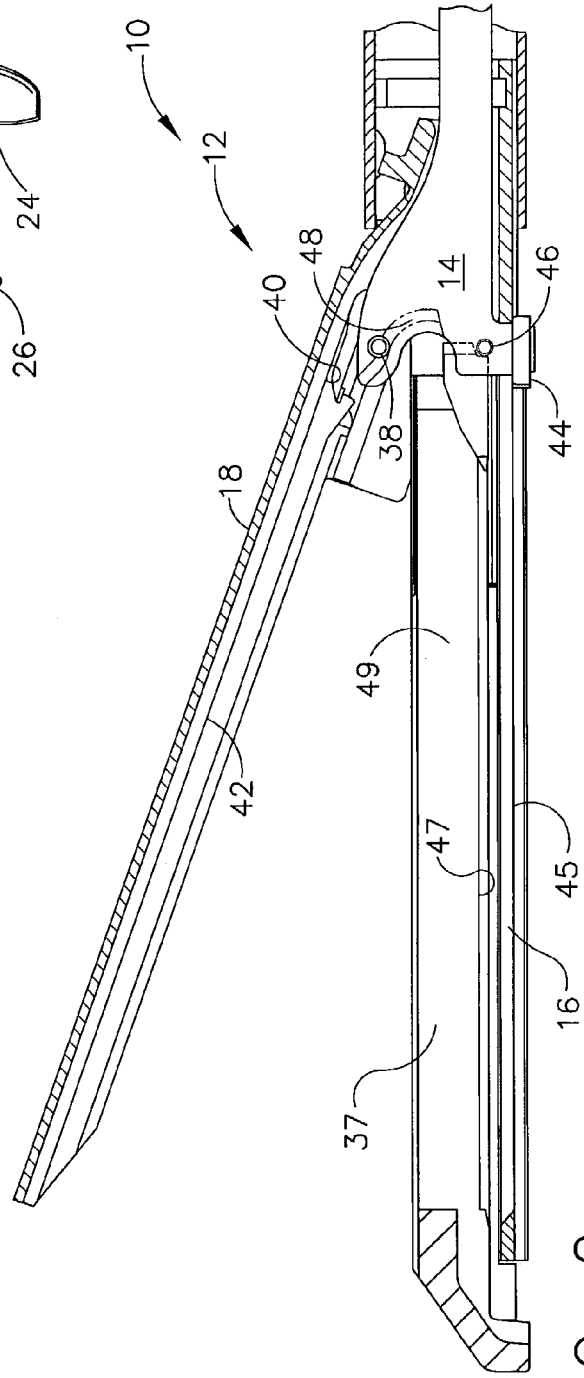
FIG. 2 depicts a cross-sectional side elevation detail view along the line 2—2 of FIG. 1 of an end effector of the surgical stapling and severing instrument.

Turning to the Drawings, wherein like numerals denote like components throughout the several views, FIGS. 1 and 2 depict a surgical stapling and severing instrument 10 that is capable of practicing the unique benefits of the present invention. The surgical stapling and severing instrument 10 incorporates an end effector 12 having an E-beam firing mechanism ("firing bar") 14 that advantageously controls the spacing of the end effector 12. In particular, an elongate channel 16 and a pivotally translatable anvil 18 are maintained at a spacing that assures effective stapling and severing. The problems are avoided associated with varying amounts of tissue being captured in the end effector 12.

The surgical and stapling and severing instrument 10 includes a handle portion 20 connected to an implement portion 22, the latter further comprising a shaft 23 distally terminating in the end effector 12. The handle portion 20 includes a pistol grip 24 toward which a closure trigger 26 is pivotally drawn by the clinician to cause clamping, or closing, of the anvil 18 toward the elongate channel 16 of the end effector 12. A firing trigger 28 is farther outboard of the closure trigger 26 and is pivotally drawn by the clinician to cause the stapling and severing of clamped tissue in the end effector 12.

It will be appreciated that the terms "proximal" and "distal" are used herein with reference to a clinician gripping a handle of an instrument. Thus, the end effector 12 is distal with respect to the more proximal handle portion 20. It will be further appreciated that for convenience and clarity, spatial terms such as "vertical" and "horizontal" are used herein with respect to the drawings. However, surgical instruments are used in many orientations and positions, and these terms are not intended to be limiting and absolute.

Closure trigger 26 is actuated first. Once the clinician is satisfied with the positioning of the end effector 12, the clinician may draw back the closure trigger 26 to its fully closed, locked position proximate to the pistol grip 24. Then, the firing trigger 28 is actuated. The firing trigger 28 springedly returns when the clinician removes pressure. A release button 30 when depressed on the proximal end of the handle portion 20 releases any locked closure trigger 26.

A closure sleeve 32 encloses a frame 34, which in turn encloses a firing drive member 36 that is positioned by the firing trigger 28. The frame 34 connects the handle portion 20 to the end effector 12. With the closure sleeve 32 withdrawn proximally by the closure trigger 26 as depicted, the anvil 18 springedly opens, pivoting away from the elongate channel 16 and translating proximally with the closure sleeve 32.

The elongate channel 16 receives a staple cartridge 37 that is responsive to the firing bar 14 to drive staples into forming contact with the anvil 18. It will appreciated that although a readily replaceable staple cartridge 37 is advantageously described herein, a staple cartridge 37 consistent with aspects of the present invention may be permanently affixed or integral to the elongate channel 16, for instance when a larger portion of the end effector 12 is replaced after each firing.

E-Beam Firing Mechanism

Figure 3:
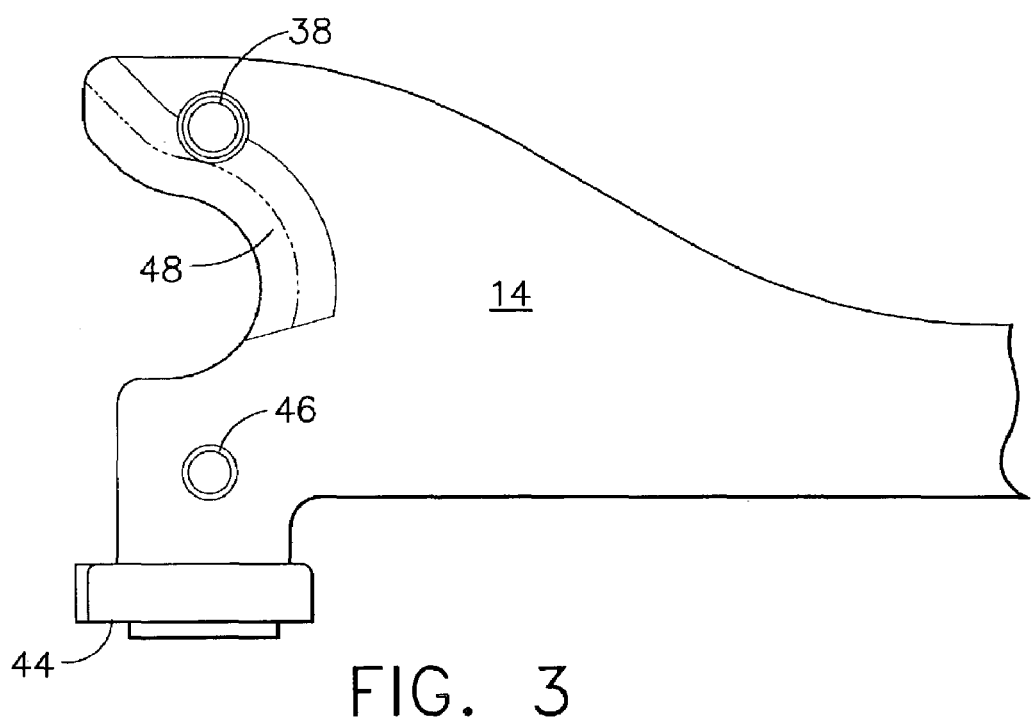
FIG. 3 depicts an enlarged side elevation view of the firing bar of the surgical stapling and severing instrument of FIG. 2.
Figure 4:
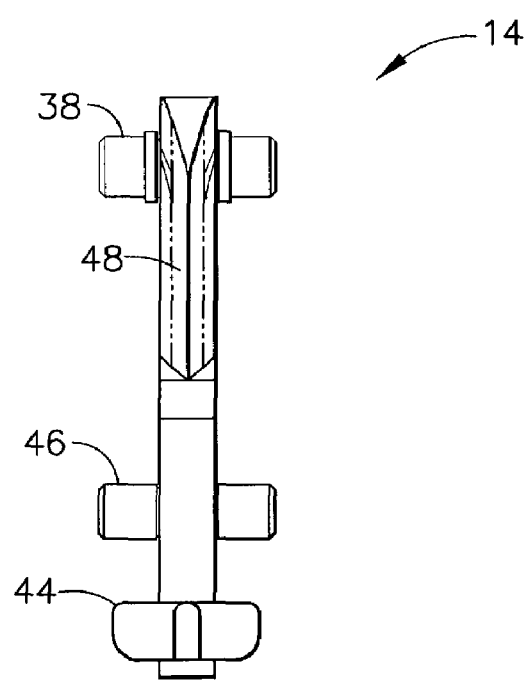
FIG. 4 depicts an enlarged front view of the firing bar of the surgical stapling and severing instrument of FIG. 2.

With particular reference to FIGS. 2–4, the firing bar 14 includes three vertically spaced pins that control the spacing of the end effector 12 during firing. In particular, an upper pin 38 is staged to enter an anvil pocket 40 near the pivot between the anvil 18 and elongate channel 16. When fired with the anvil 18 closed, the upper pin 38 advances distally within a longitudinal anvil slot 42 extending distally through anvil 18. Any minor upward deflection in the anvil 18 is overcome by a downward force imparted by the upper pin 38.

Firing bar 14 also includes a lower most pin, or firing bar cap, 44 that upwardly engages a channel slot 45 in the elongate channel 16, thereby cooperating with the upper pin 38 to draw the anvil 18 and the elongate channel 16 slightly closer together in the event of excess tissue clamped therebetween.

Figure 5:
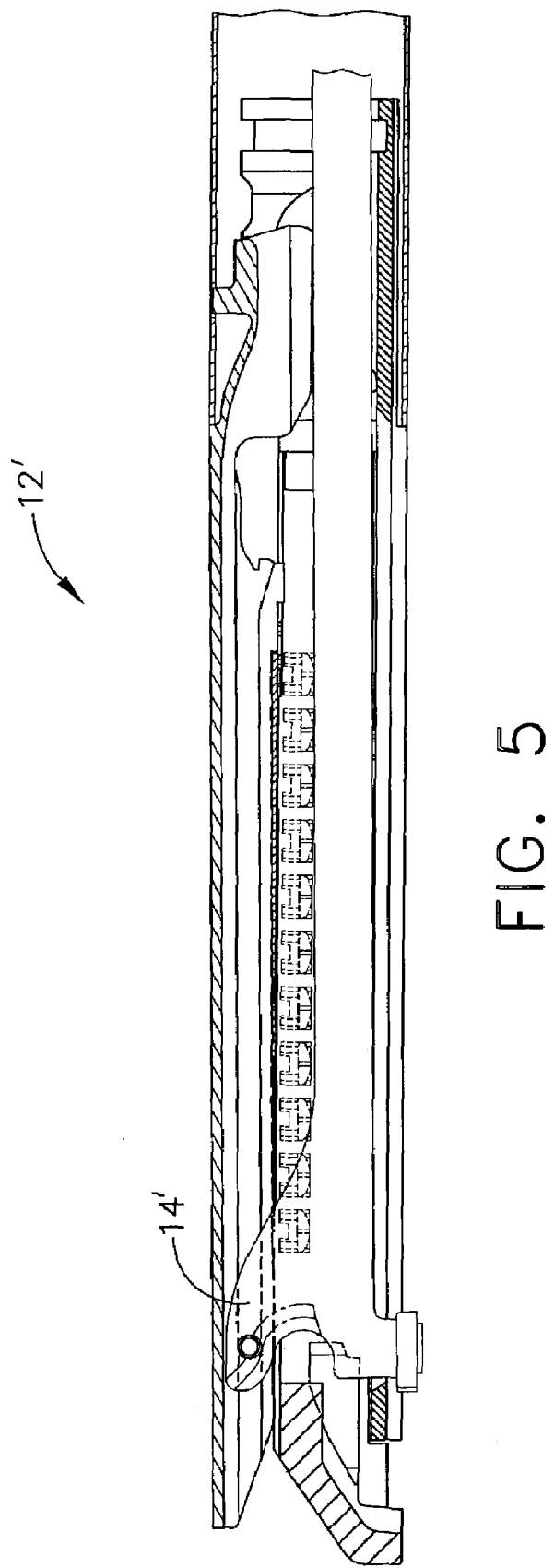
FIG. 5 depicts a cross-sectional side elevation detail view of an alternative end effector for the surgical stapling and severing instrument of FIG. 1, incorporating a firing bar that lacks a middle pin for preventing pinching of the end effector.

The firing bar 14 advantageously includes a middle pin 46 that passes through a firing drive slot 47 formed in a lower surface of the cartridge 37 and an upward surface of the elongate channel 16, thereby driving the staples therein as described below. The middle pin 46, by sliding against the elongate channel 16, advantageously resists any tendency for the end effector 12 to be pinched shut at its distal end. To illustrate an advantage of the middle pin 46, FIG. 5 depicts an alternative end effector 12' that lacks a middle pin on a firing bar 14'. In this depiction, the end effector 12' is allowed to pinch shut at its distal end, which tends to impair desired staple formation.

Returning to FIGS. 2–4, a distally presented cutting edge 48 between the upper and middle pins 38, 46 on the firing bar 14 traverses through a proximally presented, vertical slot 49 in the cartridge 37 to sever clamped tissue. The affirmative positioning of the firing bar 14 with regard to the elongate channel 16 and anvil 18 assure that an effective cut is performed.

Cambered Anvil with Selected Cartridge Gap

The affirmative vertical spacing provided by the E-Beam firing bar 14 is suitable for the limited size available for endoscopic devices. Moreover, the E-Beam firing bar 14 enables fabrication of an anvil 16 with a camber imparting a vertical deflection at its distal end, similar to the position depicted in FIG. 5. This cambered anvil 16 advantageously assists in achieving the desired gap in the end effector 12 even with an anvil 16 reduced thickness, which is thus more suited to the size limitations of an endoscopic device.

The E-Beam firing bar 14 further enables increased applications, especially in combination with a range of configurations of staple cartridges. For instance, a clinician may select a gray staple cartridge yielding a 0.02 mm tissue gap, a white staple cartridge yielding a 0.04 mm tissue gap, a blue cartridge yielding a 0.06 mm tissue gap, or a green cartridge yielding a 0.10 mm tissue gap. The vertical height of each respective staple cartridge in combination with the length of staples and an integral wedge sled (described in more detail below) predetermines this desired tissue thickness with the anvil 18 appropriately vertically spaced by the E-Beam firing bar 14.

Two-Axis Handle

With reference to FIGS. 6-9, the handle portion 20 is comprised of first and second base sections 50 and 52, which are molded from a polymeric material such as a glass-filled polycarbonate. The first base section 50 is provided with a plurality of cylindrical-shaped pins 54. The second base section 52 includes a plurality of extending members 56, each having a hexagonal-shaped opening 58. The cylindrical-shaped pins 54 are received within the hexagonal-shaped openings 58 and are frictionally held therein for maintaining the first and second base sections 50 and 52 in assembly.

A rotating knob 60 has a bore 62 extending completely through it for engaging and rotating the implement portion 22 about its longitudinal axis. The rotating knob 60 includes an inwardly protruding boss 64 extending along at least a portion of the bore 62. The protruding boss 64 is received within a longitudinal slot 66 formed at a proximal portion of the closure sleeve 32 such that rotation of the rotating knob 60 effects rotation of the closure sleeve 32. It will be appreciated that the boss 64 further extends through frame 34 and into contact with a portion of the firing drive member 36 to effect their rotation as well. Thus, the end effector 12 (not shown in FIGS. 6–9) rotates with the rotating knob 60.

A proximal end 68 of the frame 34 passes proximally through the rotating knob 60 and is provided with a circumferential notch 70 that is engaged by opposing channel securement members 72 extending respectively from the base sections 50 and 52. Only the channel securement member 72 of the second base section 52 is shown. The channel securement members 72 extending from the base sections 50, 52 serve to secure the frame 34 to the handle portion 20 such that the frame 34 does not move longitudinally relative to the handle portion 20.

The closure trigger 26 has a handle section 74, a gear segment section 76, and an intermediate section 78. A bore 80 extends through the intermediate section 78. A cylindrical support member 82 extending from the second base section 52 passes through the bore 80 for pivotably mounting the closure trigger 26 on the handle portion 20. A second cylindrical support member 83 extending from the second base section 52 passes through a bore 81 of firing trigger 28 for pivotally mounting on the handle portion 20. A hexagonal opening 84 is provided in the cylindrical support member 83 for receiving a securement pin (not shown) extending from the first base section 50.

A closure yoke 86 is housed within the handle portion 20 for reciprocating movement therein and serves to transfer motion from the closure trigger 26 to the closure sleeve 32. Support members 88 extending from the second base section 52 and securement member 72, which extends through a recess 89 in the yoke 86, support the yoke 86 within the handle portion 20.

A proximal end 90 of the closure sleeve 32 is provided with a flange 92 that is snap-fitted into a receiving recess 94 formed in a distal end 96 of the yoke 86. A proximal end 98 of the yoke 86 has a gear rack 100 that is engaged by the gear segment section 76 of the closure trigger 26. When the closure trigger 26 is moved toward the pistol grip 24 of the handle portion 20, the yoke 86 and, hence, the closure sleeve 32 move distally, compressing a spring 102 that biases the yoke 86 proximally. Distal movement of the closure sleeve 32 effects pivotal translation movement of the anvil 18 distally and toward the elongate channel 16 of the end effector 12 and proximal movement effects closing, as discussed below.

The closure trigger 26 is forward biased to an open position by a front surface 130 interacting with an engaging surface 128 of the firing trigger 28. Clamp first hook 104 that pivots top to rear in the handle portion 20 about a pin 106 restrains movement of the firing trigger 28 toward the pistol grip 24 until the closure trigger 26 is clamped to its closed position. Hook 104 restrains firing trigger 28 motion by engaging a lockout pin 107 in firing trigger 28. The hook 104 is also in contact with the closure trigger 26. In particular, a forward projection 108 of the hook 104 engages a member 110 on the intermediate section 78 of the closure trigger 26, the member 110 being outward of the bore 80 toward the handle section 74. Hook 104 is biased toward contact with member 110 of the closure trigger 26 and engagement with lockout pin 107 in firing trigger 28 by a release spring 112. As the closure trigger 26 is depressed, the hook 104 is moved top to rear, compressing the release spring 112 that is captured between a rearward projection 114 on the hook 104 and a forward projection 116 on the release button 30.

Figure 8:
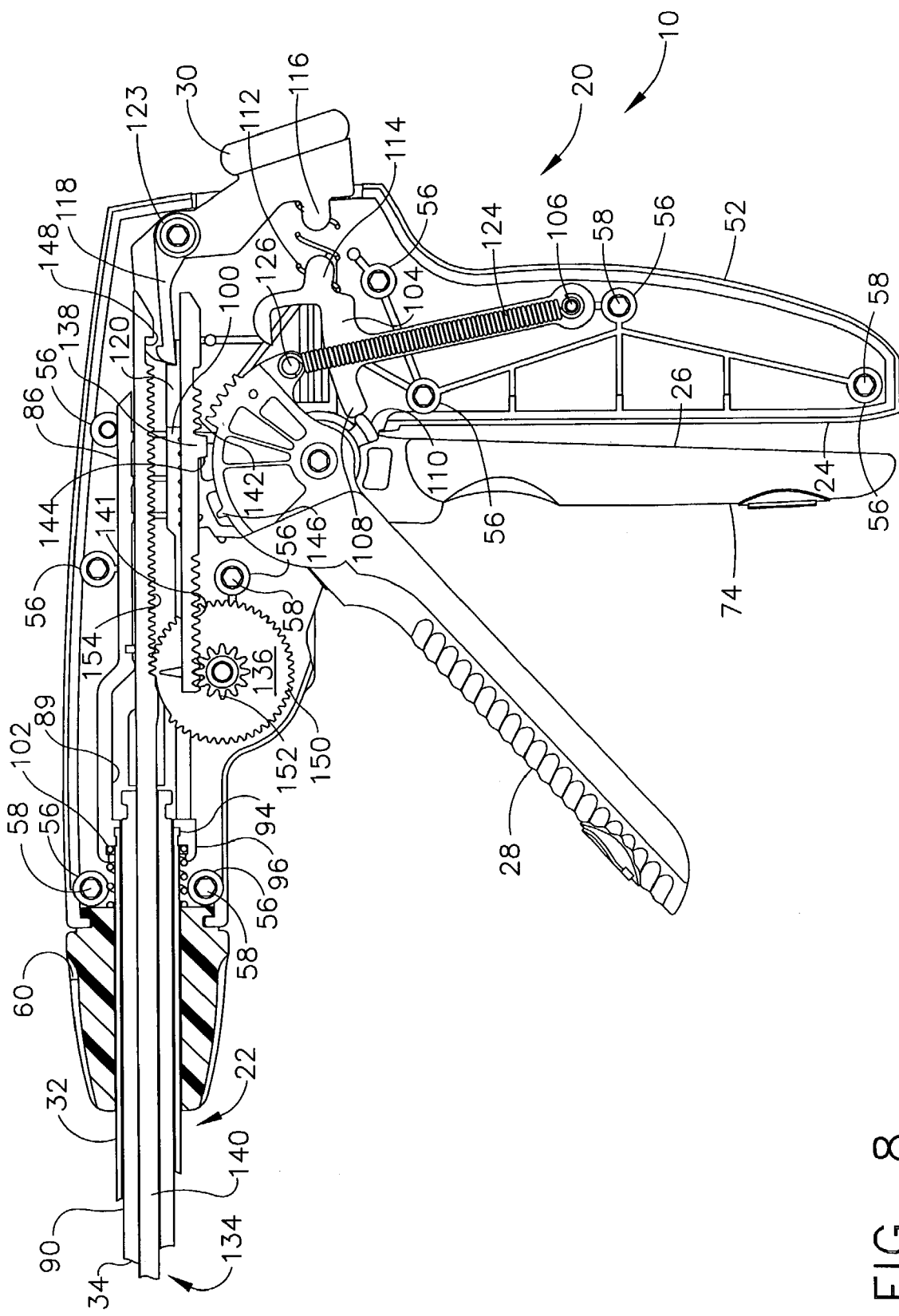
FIG. 8 depicts a side elevational view of the handle portion of the proximal end of the surgical stapling and severing instrument of FIG. 1 with the left side removed to expose interior parts in the closed ("clamped") position.

As the yoke 86 moves distally in response to proximal movement of the closure trigger 26, an upper latch arm 118 of the release button 30 moves along an upper surface 120 on the yoke 86 until dropping into an upwardly presented recess 122 in a proximal, lower portion of the yoke 86. The release spring 112 urges the release button 30 outward, which pivots the upper latch arm 118 downwardly into engagement with the upwardly presented recess 122, thereby locking the closure trigger 26 in a tissue clamping position, such as depicted in FIG. 8.

The latch arm 118 can be moved out of the recess 122 to release the anvil 18 by pushing the release button 30 inward. Specifically, the upper latch arm 118 pivots upward about pin 123 of the second base section 52. The yoke 86 is then permitted to move proximally in response to return movement of the closure trigger 26.

A firing trigger return spring 124 is located within the handle portion 20 with one end attached to pin 106 of the second base section 52 and the other end attached to a pin 126 on the firing trigger 28. The firing return spring 124 applies a return force to the pin 126 for biasing the firing trigger 28 in a direction away from the pistol grip 24 of the handle portion 20. The closure trigger 26 is also biased away from pistol grip 24 by engaging surface 128 of firing trigger 28 biasing front surface 130 of closure trigger 26.

As the closure trigger 26 is moved toward the pistol grip 24, its front surface 130 engages with the engaging surface 128 on the firing trigger 28 causing the firing trigger 28 to move to its "firing" position. When in its firing position, the firing trigger 28 is located at an angle of approximately 45° to the pistol grip 24. After staple firing, the spring 124 causes the firing trigger 28 to return to its initial position. During the return movement of the firing trigger 28, its engaging surface 128 pushes against the front surface 130 of the closure trigger 26 causing the closure trigger 26 to return to its initial position. A stop member 132 extends from the second base section 52 to prevent the closure trigger 26 from rotating beyond its initial position.

The surgical stapling and severing instrument 10 additionally includes a reciprocating section 134, a multiplier 136 and a drive member 138. The reciprocating section 134 comprises a wedge sled in the implement portion 22 (not shown in FIG. 6-9) and a metal drive rod 140.

The drive member 138 includes first and second gear racks 141 and 142. A first notch 144 is provided on the drive member 138 intermediate the first and second gear racks 141, 142. During return movement of the firing trigger 28, a tooth 146 on the firing trigger 28 engages with the first notch 144 for returning the drive member 138 to its initial position after staple firing. A second notch 148 is located at a proximal end of the metal drive rod 140 for locking the metal drive rod 140 to the upper latch arm 118 of the release button 30 in its unfired position.

The multiplier 136 comprises first and second integral pinion gears 150 and 152. The first integral pinion gear 150 is engaged with a first gear rack 154 provided on the metal drive rod 140. The second integral pinion gear 152 is engaged with the first gear rack 141 on the drive member 138. The first integral pinion gear 150 has a first diameter and the second integral pinion gear 152 has a second diameter which is smaller than the first diameter.

Figure 6:
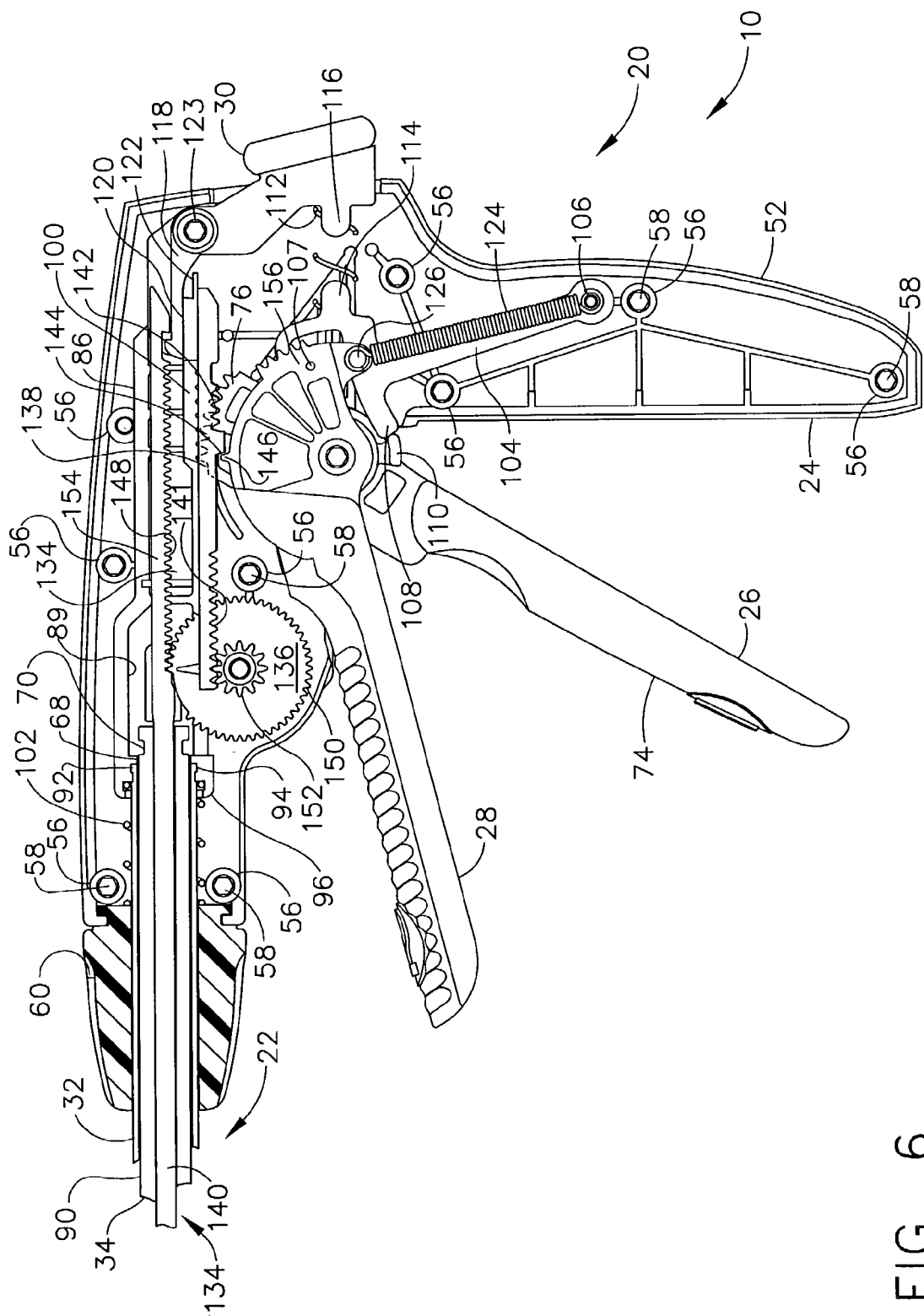
FIG. 6 depicts a side elevational view of a handle portion of a proximal end of the surgical stapling and severing instrument of FIG. 1 with a left side removed to expose interior parts in an unclamped, unfired ("start") position.
Figure 7:
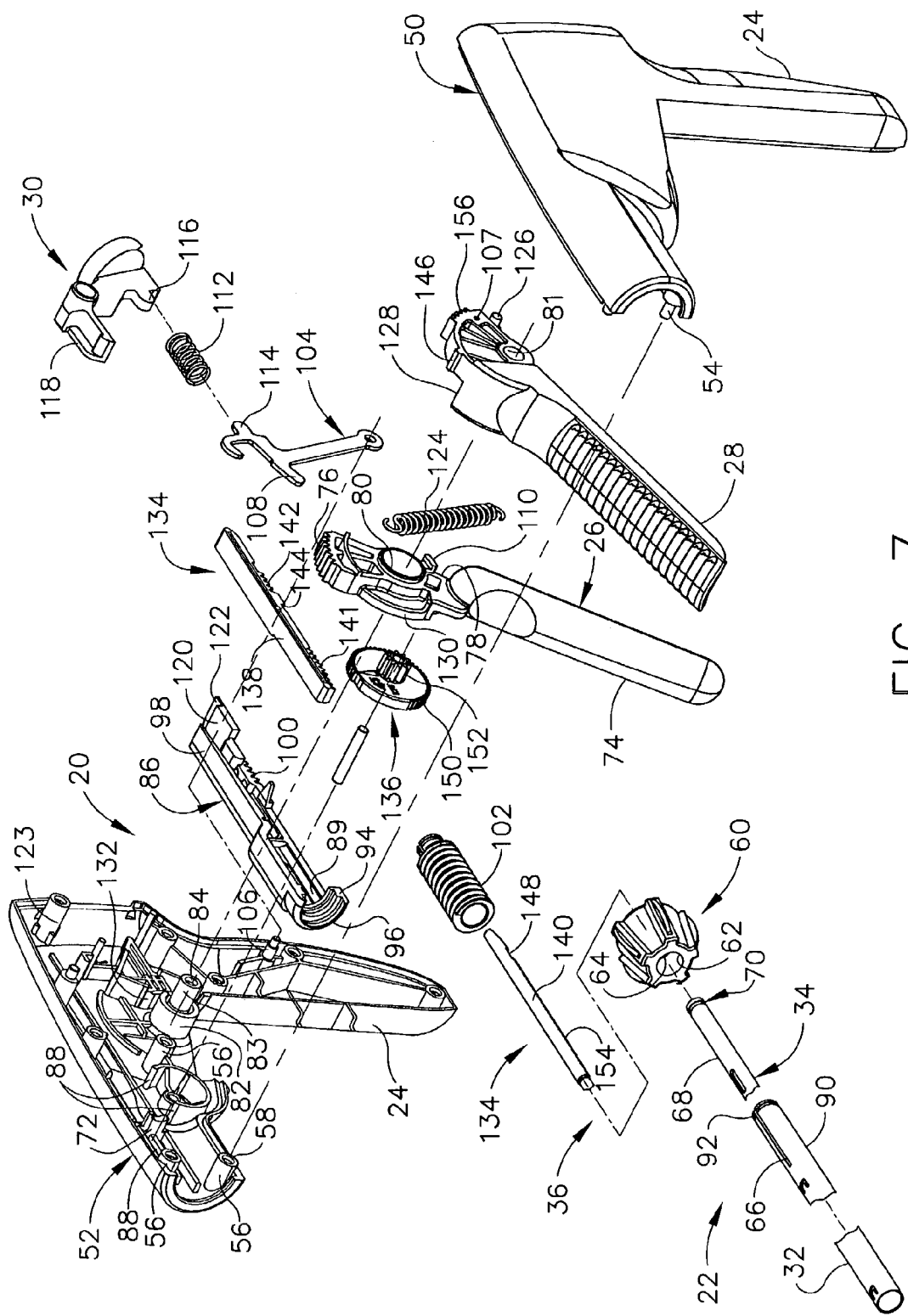
FIG. 7 depicts a perspective, exploded view of the handle portion of the proximal end of the surgical stapling and severing instrument of FIG. 1.
Figure 9:
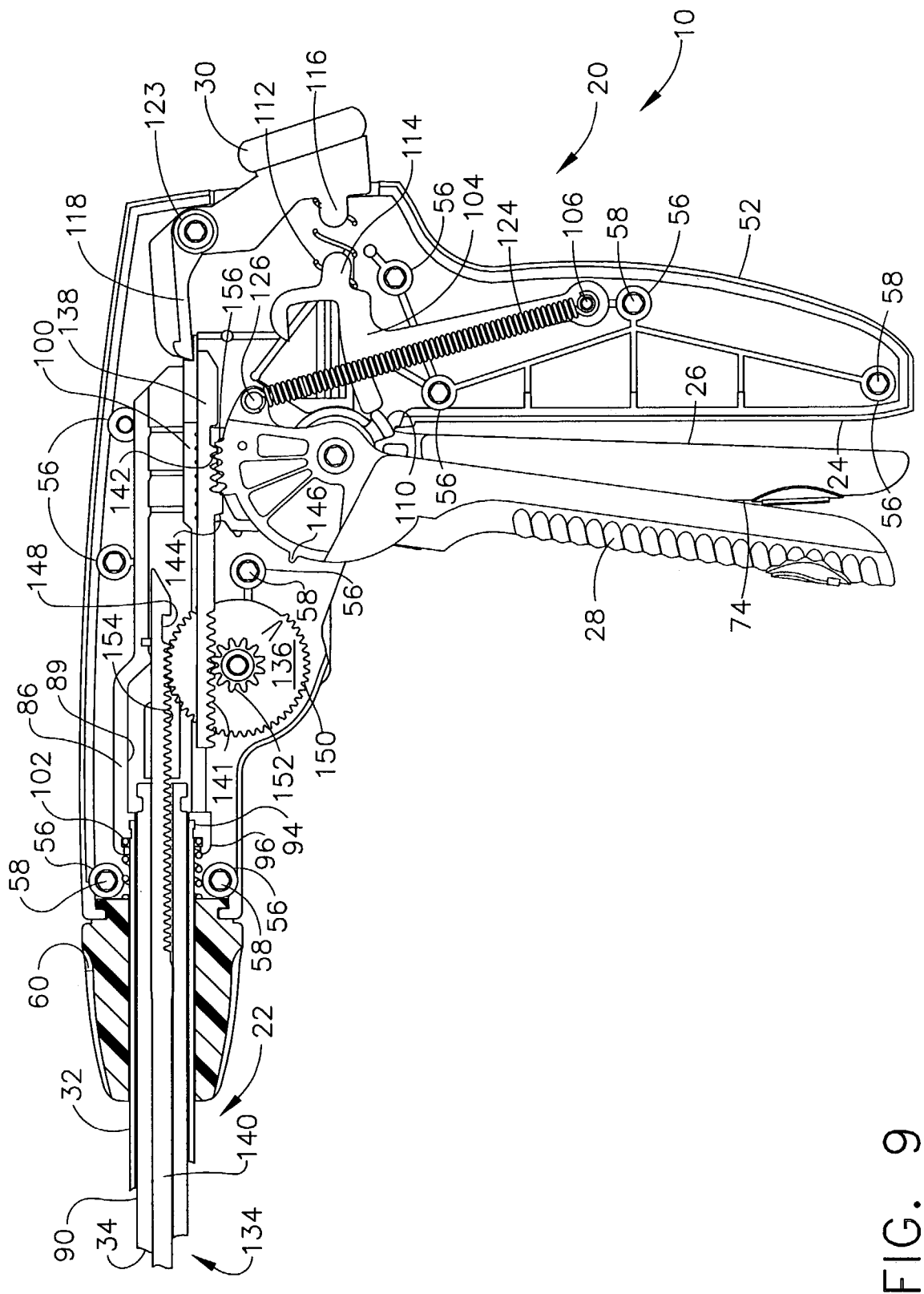
FIG. 9 depicts a side elevational view of the handle portion of proximal end of surgical stapling and severing instrument of FIG. 1 with the left side removed to expose interior parts in the stapled and severed ("fired") position.

FIGS. 6, 8 and 9 depict respectively the handle portion 20 in the start position (open and unfired), a clamped position (closed and unfired) and a fired position. The firing trigger 28 is provided with a gear segment section 156. The gear segment section 156 engages with the second gear rack 142 on the drive member 138 such that motion of the firing trigger 28 causes the drive member 138 to move back and forth between a first drive position, shown in FIG. 8, and a second drive position, shown in FIG. 9. In order to prevent staple firing before tissue clamping has occurred, the upper latch arm 118 on the release button 30 is engaged with the second notch 148 on the drive member 138 such that the metal drive rod 140 is locked in its proximal-most position, as depicted in FIG. 6. When the upper latch arm 118 falls into the recess 122, the upper latch arm 118 disengages with the second notch 148 to permit distal movement of the metal drive rod 140, as depicted in FIG. 9.

Because the first gear rack 141 on the drive member 138 and the gear rack 154 on the metal drive rod 140 are engaged with the multiplier 136, movement of the firing trigger 28 causes the metal drive rod 140 to reciprocate between a first reciprocating position, shown in FIG. 8, and a second reciprocating position, shown in FIG. 9. Since the diameter of the first pinion gear 150 is greater than the diameter of the second pinion gear 152, the multiplier 136 moves the reciprocating section 134 a greater distance than the drive member 138 is moved by the firing trigger 28. The diameters of the first and second pinion gears 150 and 152 may be changed to permit the length of the stroke of the firing trigger 28 and the force required to move it to be varied.

It will be appreciated that the handle portion 20 is illustrative and that other actuation mechanisms may be employed. For instance, the closing and firing motions may be generated by automated means.

Separate and Distinct Closing and Firing End Effector

The end effector 12 of the surgical stapling and severing instrument 10 is depicted in further detail in FIGS. 10–16. As described above, the handle portion 20 produces separate and distinct closing and firing motions that actuate the end effector 12. The end effector 12 advantageously maintains the clinical flexibility of this separate and distinct closing and firing (i.e., stapling and severing). In addition, the end effector 12 introduces the aforementioned ability to affirmatively maintain the closed spacing during firing after the clinician positions and clamps the tissue. Both features procedurally and structurally enhance the ability of the surgical stapling and severing instrument 10 by ensuring adequate spacing for instances where an otherwise inadequate amount of tissue is clamped and to enhance the clamping in instances where an otherwise excessive amount of tissue has been clamped.

Figure 10:
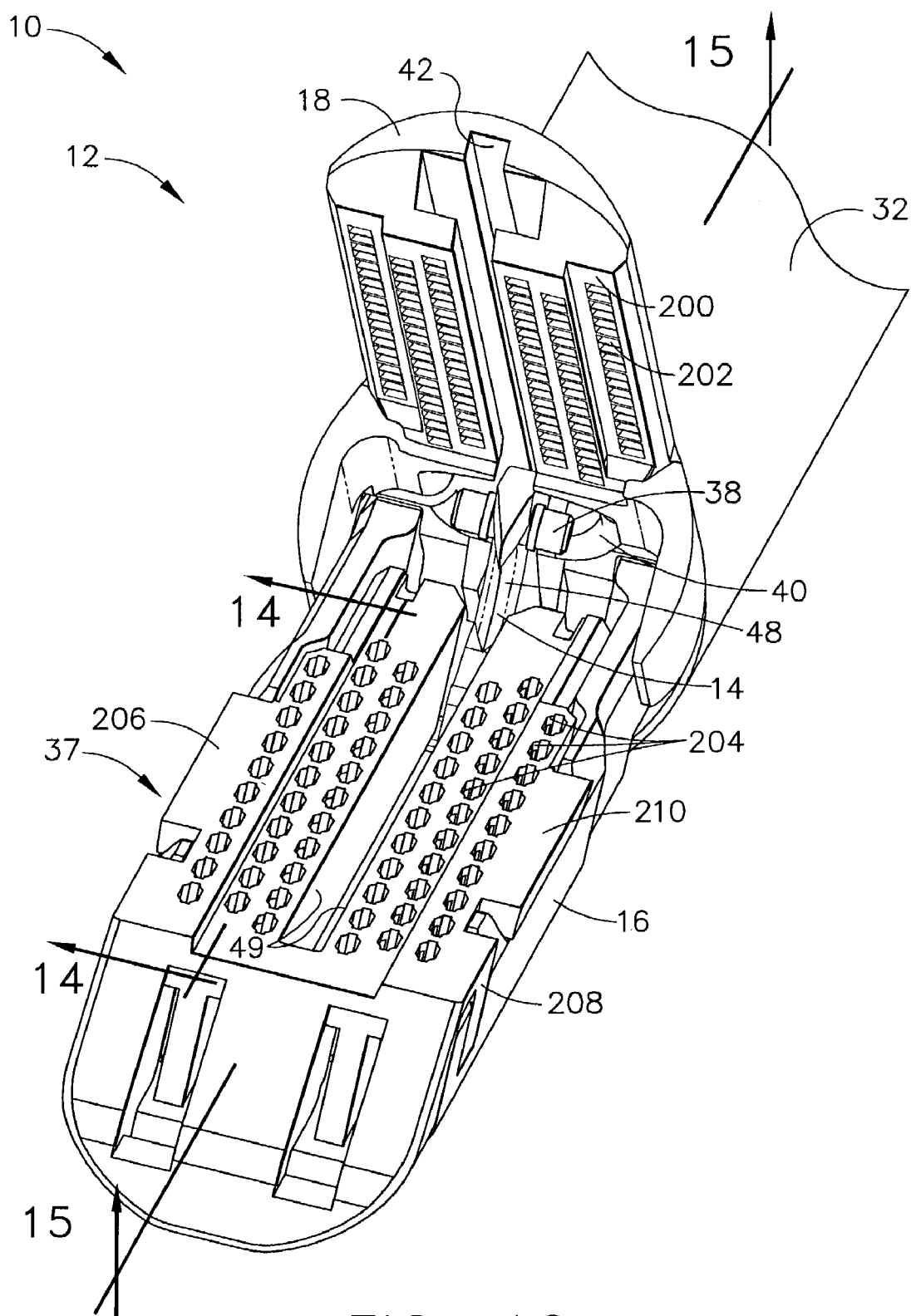
FIG. 10 depicts an isometric view of the end effector at the distal end of the surgical stapling and severing instrument of FIG. 1 with the anvil in the up or open position exposing the staple cartridge and cutting edge of the firing bar.

FIG. 10 depicts the end effector 12, which is in an open position by a retracted closure sleeve 32, with a staple cartridge 37 installed in the elongate channel 16. On a lower surface 200 of the anvil 18, a plurality of stapling forming pockets 202 are arrayed to correspond to a plurality of stapler apertures 204 in an upper surface 206 of the staple cartridge 37. The firing bar 14 is at its proximal position, with the upper pin 38 aligned in a noninterfering fashion with the anvil pocket 40. The anvil pocket 40 is shown as communicating with the longitudinal anvil slot 42 in the anvil 18. The distally presented cutting edge 48 of the firing bar 14 is aligned with and proximally from removed from the vertical slot 49 in the staple cartridge 37, thereby allowing removal of a spent cartridge and insertion of an unfired cartridge, which is snapfit into the elongate channel 16. Specifically, extension features 208, 210 of the staple cartridge 37 engage recesses 212, 214 (shown in FIG. 12) of the elongate channel 16.

Figure 11:
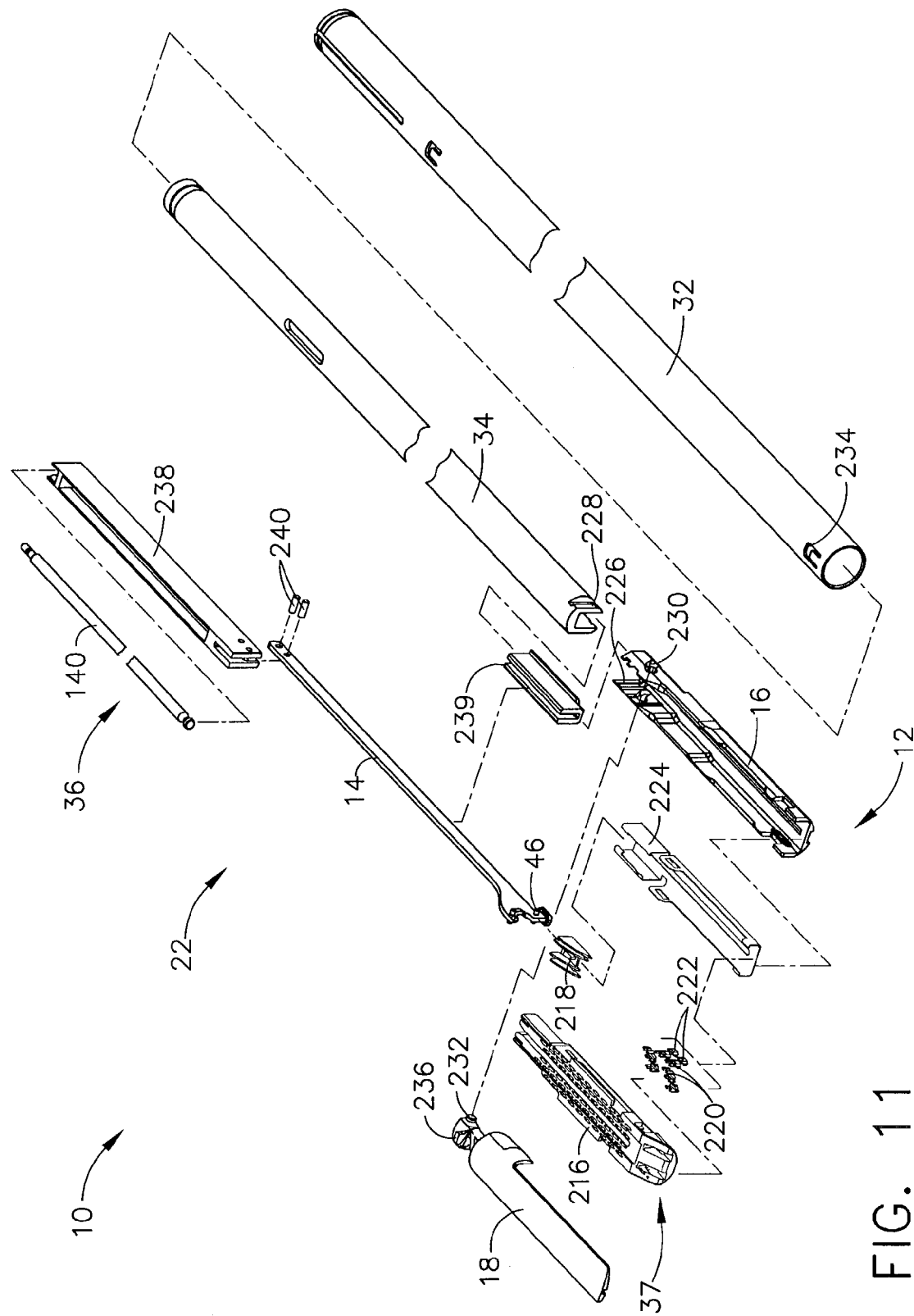
FIG. 11 depicts an isometric, exploded view of the implement portion of the surgical stapling and severing instrument of FIG. 1.

FIG. 11 shows the implement portion 22 of the surgical stapling and severing instrument 10 in disassembled form. The staple cartridge 37 is shown as being comprised of a cartridge body 216, a wedge sled 218, single and double drivers 220, staples 222, and a cartridge tray 224. When assembled, the cartridge tray 224 holds the wedge sled 218, single and double drivers 220, and staples 222 inside the cartridge body 216.

Having a wedge sled 218 integral to the staple cartridge 37 enables a number of flexible design options as compared to incorporating camming surfaces onto a firing bar itself. For instance, a number of different staple cartridges may be selected for use in the instrument 10 with each staple cartridge having a different configuration of rows of staples, each thus having a unique wedge sled configured to contact the middle pin 46 of the firing bar 14 while causing the driving of the staples 222. As another example, the integral wedge sled 218 provides an opportunity for a number of lockout features, described in greater detail in the first and third aforementioned co-pending applications.

The elongate channel 16 has a proximally placed attachment cavity 226 that receives a channel anchoring member 228 on the distal end of the frame 34 for attaching the end effector 12 to the handle portion 20. The elongate channel 16 also has an anvil cam slot 230 that pivotally receives an anvil pivot 232 of the anvil 18. The closure sleeve 32 that encompasses the frame 34 includes a distally presented tab 234 that engages an anvil feature 236 proximate but distal to the anvil pivot 232 on the anvil 18 to thereby effect opening and closing of the anvil 18. The firing drive member 36 is shown as being assembled from the firing bar 14 attached to a firing connector 238 by pins 240, which in turn is rotatingly and proximally attached to the metal drive rod 140. The firing bar 14 is guided at a distal end of the frame by a slotted guide 239 inserted therein.

Figure 12:
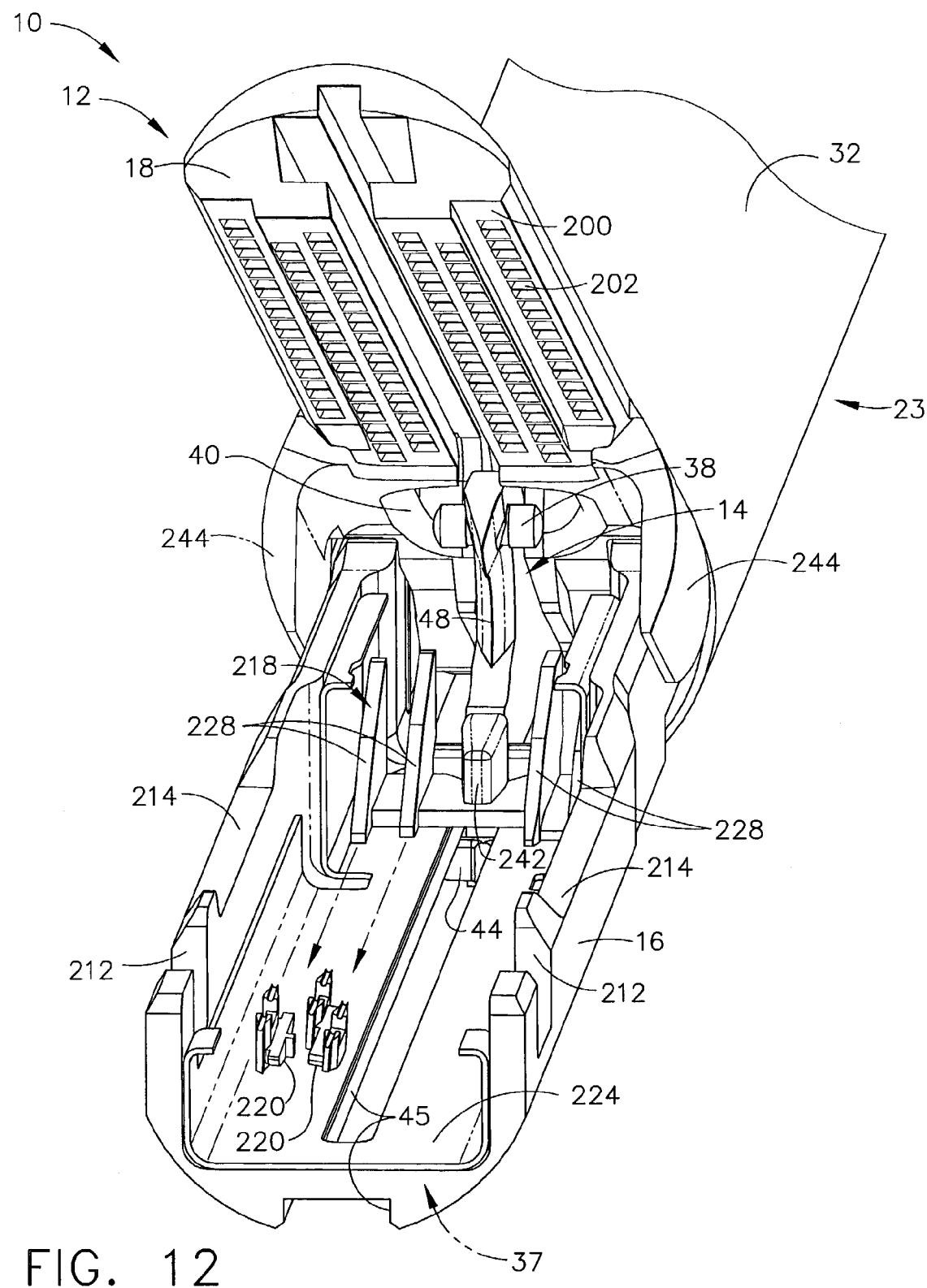
FIG. 12 depicts an isometric view of the end effector at the distal end of the surgical stapling and severing instrument of FIG. 1 with the anvil in the up or open position with the cartridge largely removed exposing a single staple driver and a double staple driver as exemplary and the wedge sled in its start position against a middle pin of the firing bar.

With particular reference to FIG. 12, a portion of the staple cartridge 37 is removed to expose portions of the elongate channel 16, such as recesses 212, 214 and to expose some components of the staple cartridge 37 in their unfired position. In particular, the cartridge body 216 (shown in FIG. 11) has been removed. The wedge sled 218 is shown at its proximal, unfired position with a pusher block 242 contacting the middle pin 46 (not shown in FIG. 12) of the firing bar 14. The wedge sled 218 is in longitudinal sliding contact upon the cartridge tray 224 and includes wedges 228 that force upward the single and double drivers 220 as the wedge sled 218 moves distally. Staples 222 (not shown in FIG. 12) resting upon the drivers 220 are thus also forced upward into contact with the anvil forming pockets 202 on the anvil 18 to form closed staples. Also depicted is the channel slot 45 in the elongate channel 16 that is aligned with the vertical slot 49 in the staple cartridge 37.

Figure 13:
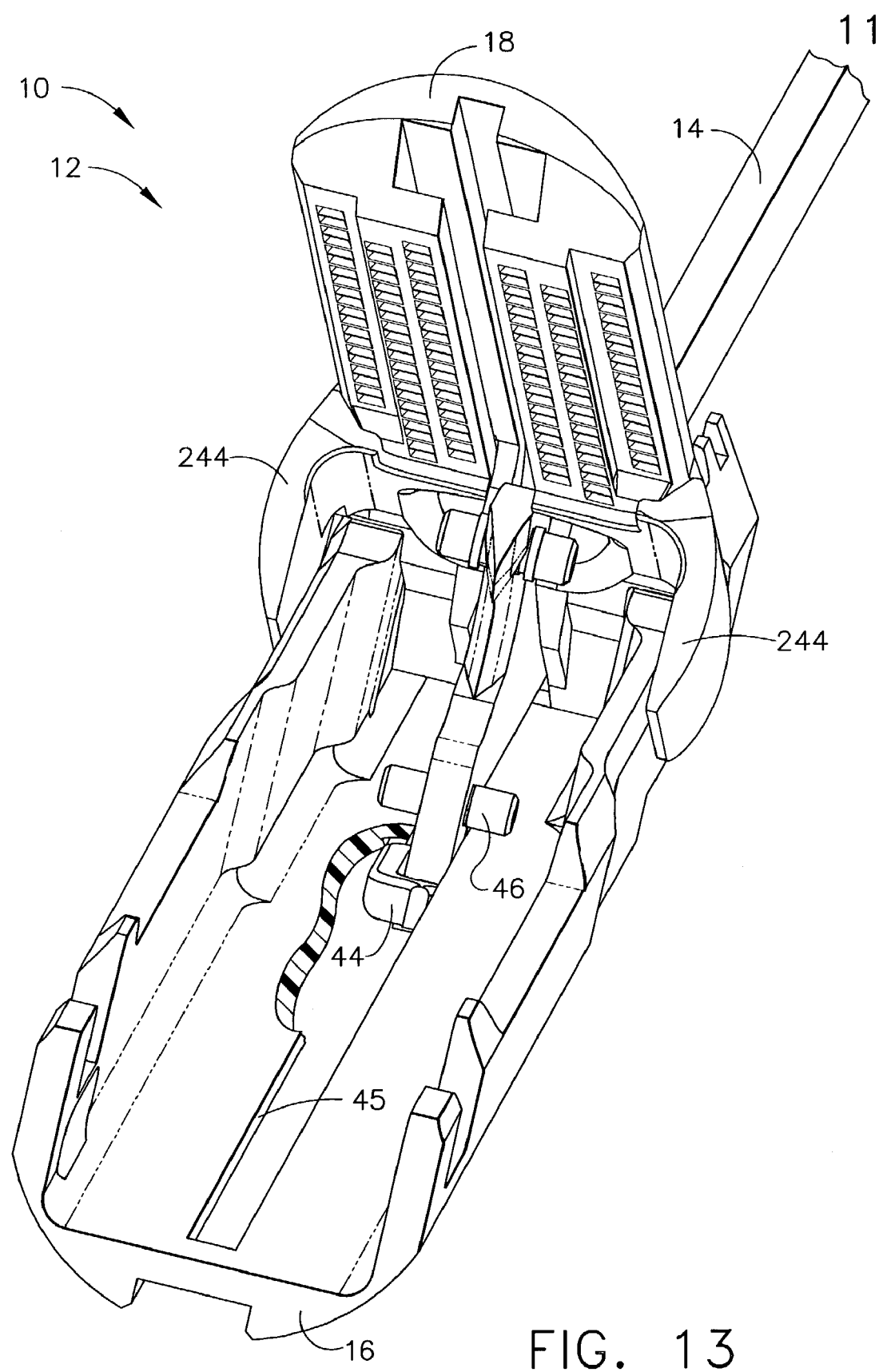
FIG. 13 depicts an isometric view of the distal end of the surgical stapling and severing instrument of FIG. 1 with the anvil in the up or open position with the staple cartridge completely removed and a portion of an elongate channel removed to expose a lowermost pin of the firing bar.

FIG. 13 depicts the end effector 12 of FIG. 12 with all of the staple cartridge 37 removed to show the middle pin 46 of the firing bar 14 as well as portion of the elongate channel 16 removed adjacent to the channel slot 45 to expose the firing bar cap 44. In addition, portions of the shaft 23 are removed to expose a proximal portion of the firing bar 14. Projecting downward from the anvil 18 near the pivot, a pair of opposing tissue stops 244 prevent tissue being positioned too far up into the end effector 12 during clamping.

Figure 14:
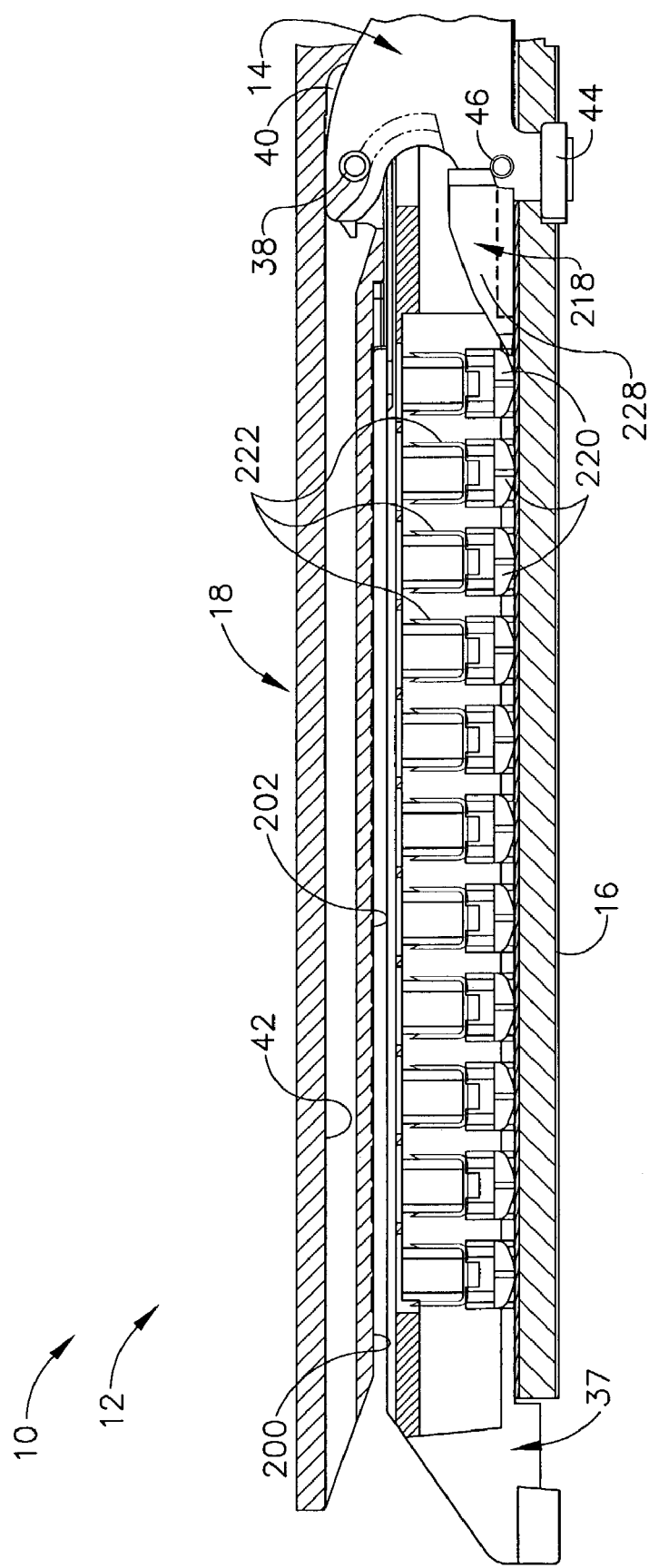
FIG. 14 depicts a side elevation view in section showing a mechanical relationship between the anvil, elongate channel, and staple cartridge in the closed position of the surgical stapling and severing instrument of FIG. 1, the section generally taken along lines 14—14 of FIG. 10 to expose wedge sled, staple drivers and staples but also depicting the firing bar along the longitudinal centerline.

FIG. 14 depicts the end effector 12 closed in a tissue clamping position with the firing bar 14 unfired. The upper pin 38 is in the anvil pocket 40, vertically aligned with the anvil slot 42 for distal longitudinal movement of the firing bar 14 during firing. The middle pin 46 is positioned to push the wedge sled 218 distally so that wedge 228 sequentially contacts and lifts double drivers 220 and the respective staples 222 into forming contact with staple forming pockets 202 in the lower surface 200 of the anvil 18.

FIG. 15 depicts the upper surface 206 of the staple cartridge 37 with the firing bar 14 in its unfired, proximal position. The stapler apertures 204 are arrayed on each side of the vertical slot 49 in the staple cartridge 37.

FIG. 16 depicts the end effector 12 near the pivot showing that the elongate channel 16 has opposing ramp portions 246 to thereby cooperate with the tissue stops 244 of the anvil 18 (not shown in FIG. 16) to prevent tissue from jamming the end effector 12. Also depicted in greater detail are the double drivers 220 and their relation to the staples 222.

Operation

Figure 17:
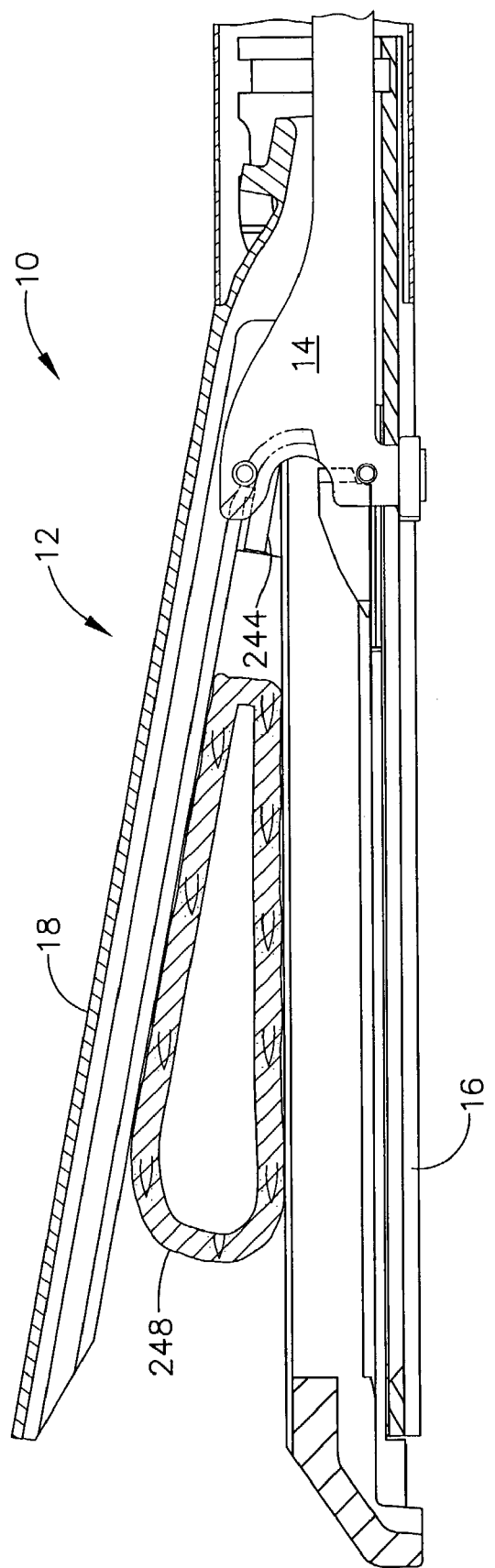
FIG. 17 depicts a side elevation section view of the surgical stapling and severing instrument of FIG. 1 taken along the longitudinal centerline of the end effector in a partially closed but unclamped position gripping tissue.

In use, the surgical stapling and severing instrument 10 is used as depicted in FIGS. 1, 2, and 17–23. In FIGS. 1–2, the instrument 10 is in its start position, having had an unfired, fully loaded staple cartridge 37 snap-fitted into the distal end of the elongate channel 16. Both triggers 26, 28 are forward and the end effector 12 is open, such as would be typical after inserting the end effector 12 through a trocar or other opening into a body cavity. The instrument 10 is then manipulated by the clinician such that tissue 248 to be stapled and severed is positioned between the staple cartridge 37 and the anvil 18, as depicted in FIG. 17.

Figure 18:
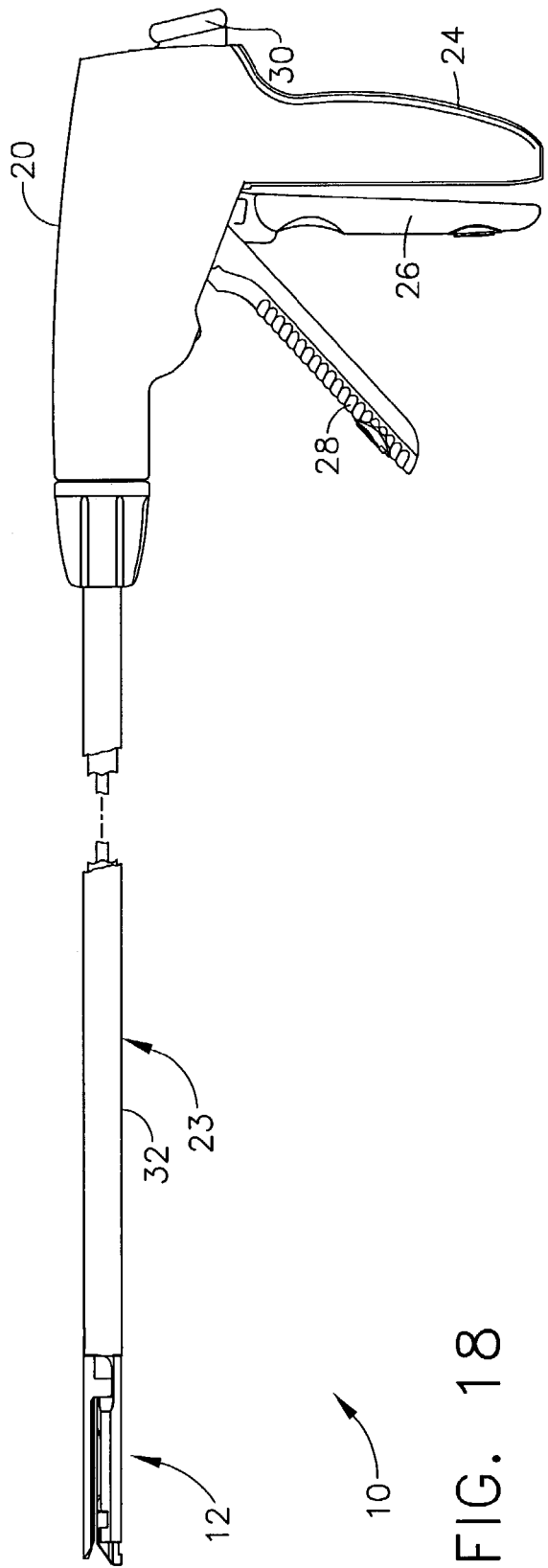
FIG. 18 depicts a partially cut-away side elevational view of the surgical stapling and severing instrument of FIG. 1 in the closed or clamped position.
Figure 19:
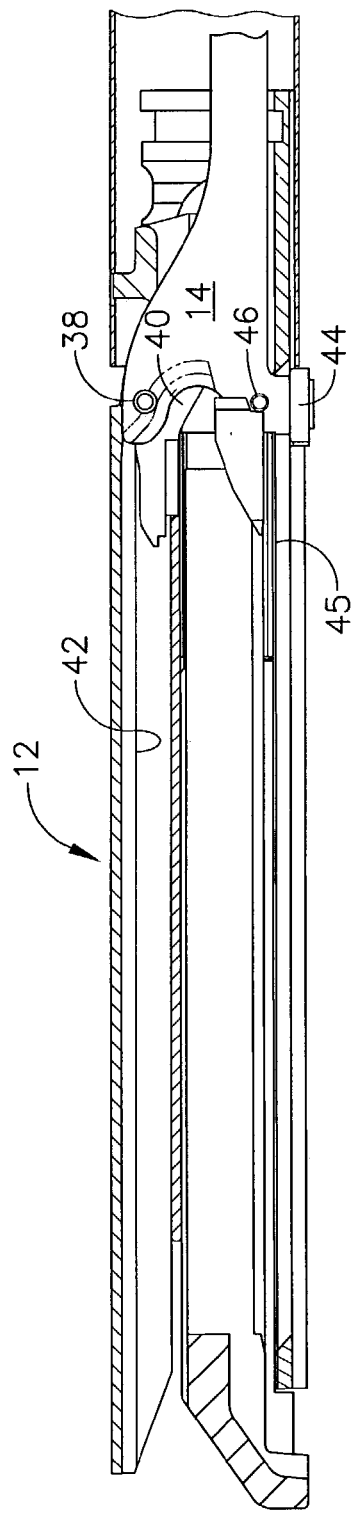
FIG. 19 depicts a side elevation view in centerline section of the distal end of the surgical stapling and severing instrument of FIG. 1 in the closed or clamped position with tissue properly compressed.

With reference to FIGS. 18–19, next, the clinician moves the closure trigger 26 proximally until positioned directly adjacent to the pistol grip 24, locking the handle portion 20 into the closed and clamped position. The retracted firing bar 14 in the end effector 12 does not impede the selective opening and closing of the end effector 12, but rather resides within the anvil pocket 40. With the anvil 18 closed and clamped, the E-beam firing bar 14 is aligned for firing through the end effector 12. In particular, the upper pin 38 is aligned with the anvil slot 42 and the elongate channel 16 is affirmatively engaged about the channel slot 45 by the middle pin 46 and the firing bar cap 44.

Figure 20:
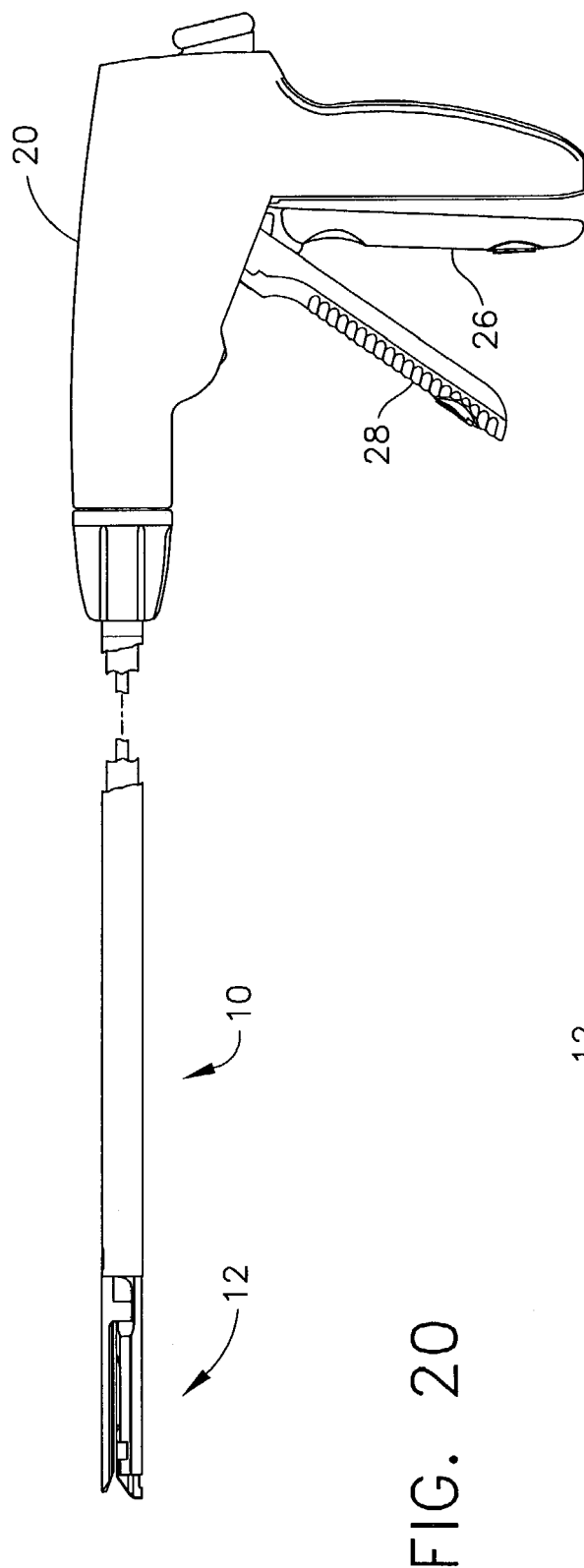
FIG. 20 depicts a partially cut-away side elevation view of the surgical stapling and severing instrument of FIG. 1 in a partially fired position.
Figure 21:
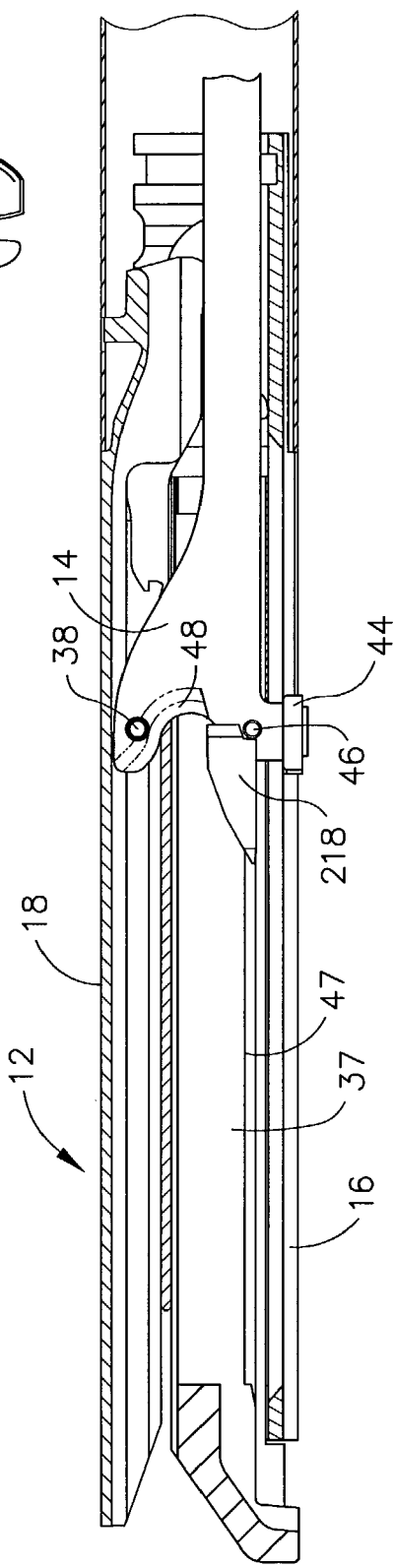
FIG. 21 depicts a view in centerline section of the distal end of the surgical stapling and severing instrument of FIG. 1 in a partially fired position.

With reference to FIGS. 20–21, after tissue clamping has occurred, the clinician moves the firing trigger 28 proximally causing the firing bar 14 to move distally into the end effector 12. In particular, the middle pin 46 enters the staple cartridge 37 through the firing drive slot 47 to effect the firing of the staples 222 (not shown in FIGS. 20–21) via wedge sled 218 toward the anvil 18. The lower most pin, or firing bar cap 44, cooperates with the middle pin 46 to slidingly position cutting edge 48 of the firing bar 14 to sever tissue. The two pins 44, 46 also position the upper pin 38 of the firing bar 14 within longitudinal anvil slot 42 of the anvil 18, affirmatively maintaining the spacing between the anvil 18 and the elongate channel 16 throughout its distal firing movement.

With reference to FIGS. 22–23, the clinician continues moving the firing trigger 28 until brought proximal to the closure trigger 26 and pistol grip 24. Thereby, all of the ends of the staples 222 are bent over as a result of their engagement with the anvil 18. The firing bar cap 44 is arrested against a firing bar stop 250 projecting toward the distal end of the channel slot 45. The cutting edge 48 has traversed completely through the tissue. The process is complete by releasing the firing trigger 28 and by then depressing the release button 30 while simultaneously squeezing the closure trigger 26 to open the end effector 12.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, the affirmative spacing of the anvil 18 and elongate channel 16 is achieved in part with two pins 44, 46 on the firing bar 14 engaging opposite sides of a channel slot 47 and a single upper pin 38 entrained within an anvil slot 42. It would consistent with aspects of the invention for the anvil to be captured by opposing pins on either side of a longitudinal slot and/or for an elongate channel to have an internal slot that entrains a lower pin.

For another example, although the E-beam firing beam 14 has advantages for an endoscopically employed surgical severing and stapling instrument 10, a similar E-Beam may be used in other clinical procedures. It is generally accepted that endoscopic procedures are more common than laparoscopic procedures. Accordingly, the present invention has been discussed in terms of endoscopic procedures and apparatus. However, use herein of terms such as "endoscopic", should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures.

For yet another example, although an illustrative handle portion 20 described herein is manually operated by a clinician, it is consistent with aspects of the invention for some or all of the functions of a handle portion to be powered (e.g., pneumatic, hydraulic, electromechanical, ultrasonic, etc.). Furthermore, controls of each of these functions may be manually presented on a handle portion or be remotely controlled (e.g., wireless remote, automated remote console, etc.).

As yet an additional example, although a simultaneous stapling and severing instrument is advantageously illustrated herein, it would be consistent with aspects of the invention for stapling to comprise other types of fasteners and attachment techniques.

What is claimed is:

1. A surgical instrument comprising:
   a handle portion operable to produce a firing motion;
   an implement portion responsive to the firing motions from the handle portion, the implement portion comprising:
   an elongate channel coupled to the handle portion and including a channel slot, a staple cartridge received by the elongate channel and incorporating a proximally positioned wedge member aligned to cam upward a driver supporting a staple, an anvil pivotally coupled to the elongate channel and including an anvil channel comprising a vertical slot inwardly open along a longitudinal axis of the anvil and comprising left and right rectanaular prism-shaped recesses communicating with, bisected by, and transverse to the vertical slot, wherein said left and right rectangular prism-shaped recesses extend substantially along the longitudinal length of the vertical slot, a firing device including a distally presented cutting edge longitudinally received between the elongate channel and the vertical slot of the anvil channel of the anvil, an upper member comprised of left and right lateral upper pins sized to slidingly engage upper and lower inner surfaces of the left and right rectangular-shaped recesses of the anvil channel, a lower member engaging the channel slot, and a middle member operable to actuate the staple cartridge by distally translating the wedge member of the staple cartridge, the firing device positively engaging both the elongate channel and the anvil during longitudinal firing travel to provide spacing therebetween for staple formation, and wherein engagement of the firing device during firing maintains vertical spacing between the elongate channel and the anvil resisting both pinching due to an inadequate clamped tissue and partial opening due to an excessive amount of clamped tissue.

2. The surgical instrument of claim 1, wherein the anvil forms an inwardly biased relation to the elongate channel configured to assist the firing device in affirmatively spacing between the anvil and elongate channel during actuation of the staple cartridge.

3. The surgical instrument of claim 2, further comprising a closure member operatively configured to longitudinally transfer the closure motion to the implement portion to inwardly bias distal ends of the anvil and the elongate channel to assist the firing device in affirmatively spacing the anvil and elongate channel during actuation of the staple cartridge.

4. The surgical instrument of claim 1, wherein the staple cartridge is a selected type of a plurality of staple cartridge types, each staple cartridge type characterized by a thickness selected for a desired spacing between the anvil and elongate channel and characterized by staples having a length suitable for the desired spacing.

5. The surgical instrument of claim 4, wherein the wedge member comprises a wedge sled having a plurality of connected camming wedges each having a preselected height configured for the selected type of staple cartridge, the middle member of the firing device oriented to abut each of the plurality of staple cartridge types.

6. A surgical instrument comprising:
a handle portion operable to produce a firing motion and a closing motion; and
an implement portion responsive to the firing motions from the handle portion and diametrically dimensioned for endo-surgical use, the implement portion comprising:
a shaft coupled to the handle portion operable to separately transfer the firing motion and the closing motion,
an elongate channel coupled to the shaft and including a channel slot,
an anvil pivotally coupled to the elongate channel, responsive to the closing motion from the shaft, and including an anvil channel, and
a firing device including a distally presented cutting edge longitudinally received between the elongate channel and the anvil, the firing device configured to affirmatively space the anvil from the elongate channel during longitudinal travel between the anvil and elongate channel,
wherein the firing device is configured to affirmatively space the anvil from the elongate channel during longitudinal travel between the anvil and elongate channel by including an upper member having an upper surface and a lower surface that longitudinally slidingly engage the anvil.

7. The surgical instrument of claim 6, further comprising a staple cartridge engaged by the elongate channel and including a proximally opened slot for receiving the cutting edge of the firing device, the staple cartridge including a plurality of staples cammed upwardly by the distal longitudinal movement of the firing mechanism.

8. The surgical instrument of claim 7, wherein the staple cartridge further includes a plurality of drivers supporting the plurality of staples and a wedge sled responsive to the distal longitudinal movement of the firing mechanism to cam upwardly the drivers and thus form the plurality of staples against the anvil.

9. The surgical instrument of claim 7, wherein the anvil forms an inwardly biased relation to the elongate channel configured to assist the firing device in affirmatively spacing between the anvil and elongate channel during actuation of the staple cartridge.

10. The surgical instrument of claim 7, wherein the staple cartridge is a selected type of a plurality of staple cartridge types, each staple cartridge type characterized by a thickness selected for a desired spacing between the anvil and elongate channel and characterized by staples having a length suitable for the desired spacing.

11. The surgical instrument of claim 10, wherein the wedge sled comprises a plurality of connected camming wedges each having a preselected height configured for the selected type of staple cartridge, the middle member of the firing device oriented to abut each of the plurality of staple cartridge types.

12. The surgical instrument of claim 6, wherein the anvil includes a longitudinal slot having an upper surface and a lower surface that slidingly abut respectively the lower surface and upper surface of the upper member of the firing device.

13. The surgical instrument of claim 12, wherein the longitudinal slot comprises an internal longitudinal channel communicating with a narrowed vertical slot, and wherein the firing device translates in the narrowed vertical slot and includes an upper member having the upper and lower surfaces that reside within the internal longitudinal channel for affirmatively spacing the anvil from the elongate channel.

14. The surgical instrument of claim 6, wherein the firing device is configured to affirmatively space the anvil from the elongate channel during longitudinal travel between the anvil and elongate channel by including a lower portion having an upper surface and a lower surface that slidingly engage the elongate channel.

15. The surgical instrument of claim 14, wherein the lower portion of the firing device comprises a lower pin having the upper surface abutting the elongate channel and comprises a middle pin having the lower surface opposingly abutting the elongate channel.

16. The surgical instrument of claim 15, wherein the firing device further comprises an upper member having an upper surface and a lower surface that longitudinally slidingly engage the anvil.

17. The surgical instrument of claim 16, wherein the anvil includes an internal longitudinal slot having a narrowed vertical slot, and wherein the firing device translates in the narrowed vertical slot and includes an upper member having upper and lower surfaces that reside within the internal longitudinal slot for affirmatively spacing the anvil from the elongate channel.

* * * * *

UNITED STATES PATENT AND TRADEMARK OFFICE
CERTIFICATE OF CORRECTION

PATENT NO.    : 6,978,921 B2                                       Page 1 of 1
DATED         : December 27, 2005
INVENTOR(S)   : Frederick E. Shelton, IV, Michael Earl Setser and William Bruce Weisenburgh, II It is certified that error appears in the above-identified patent and that said Letters Patent is hereby corrected as shown below:

<u>Title page,</u>
Item [57], ABSTRACT,
Line 1, "instrument clamps" should be -- instrument clamp --.
Line 5, "affirmatively spaces the spaces the anvil" should be -- affirmatively spaces the anvil --.

Signed and Sealed this

Second Day of May, 2006

JON W. DUDAS
*Director of the United States Patent and Trademark Office*